(12) United States Patent
Johnson et al.

(10) Patent No.: US 11,714,078 B1
(45) Date of Patent: Aug. 1, 2023

(54) SYSTEMS AND METHODS FOR DETERMINING GROUND WATER-SURFACE WATER INTERACTIONS

(71) Applicant: Battelle Memorial Institute, Richland, WA (US)

(72) Inventors: Timothy C. Johnson, Richland, WA (US); Christopher E. Strickland, Ellensburg, WA (US); Yue Zhu, Richland, WA (US); Jonathan N. Thomle, West Richland, WA (US); James C. Stegen, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 950 days.

(21) Appl. No.: 16/438,312

(22) Filed: Jun. 11, 2019

Related U.S. Application Data

(60) Provisional application No. 62/683,944, filed on Jun. 12, 2018.

(51) Int. Cl.
| | |
|---|---|
| *G01N 33/24* | (2006.01) |
| *G01L 19/00* | (2006.01) |
| *G01K 13/02* | (2021.01) |
| *G01N 15/08* | (2006.01) |
| *G01N 15/00* | (2006.01) |

(Continued)

(52) U.S. Cl.
CPC ........... *G01N 33/246* (2013.01); *G01K 13/02* (2013.01); *G01K 13/12* (2013.01); *G01L 19/0092* (2013.01); *G01L 19/083* (2013.01); *G01N 15/088* (2013.01); *G01R 27/22* (2013.01); *G01K 13/026* (2021.01); *G01N 2015/0034* (2013.01); *G01N 2015/0833* (2013.01); *G01N 2030/0095* (2013.01); *G01V 2210/661* (2013.01)

(58) Field of Classification Search
CPC ......... G01N 33/246; G01N 2015/0034; G01N 15/088; G01N 2015/0833; G01N 15/08; G01K 13/026; G01L 19/0092
See application file for complete search history.

(56) References Cited

U.S. PATENT DOCUMENTS

| | | | |
|---|---|---|---|
| 9,772,423 B2 | 9/2017 | Johnson | |
| 2010/0198547 A1* | 8/2010 | Mulligan | .............. E21B 49/001 |
| | | | 702/100 |

OTHER PUBLICATIONS

Anderson, "Heat as a Ground Water Tracer", Ground Water vol. 43(6), 2005, United States, 18 pages.

(Continued)

*Primary Examiner* — Paul M. West
(74) *Attorney, Agent, or Firm* — Wells St. John P.S.

(57) ABSTRACT

Systems for determining GW/SW interaction are provided. The systems can include: a sensing assembly comprising sensors for pressure, fluid conductivity, temperature, and transfer resistance; processing circuitry operatively coupled to the sensing assembly and configured to receive data from the sensing assembly and process the data to provide a GW/SW interaction, wherein the data includes pressure, fluid conductivity, temperature, transfer resistance data. Methods for determining GW/SW interaction are provided. The methods can include: receiving real time data including pressure, fluid conductivity, temperature, and transfer resistance; from at least some of the data received simulating the SW/GW interaction; and fitting the real time data with the simulated data to provide actual SW/GW interaction.

15 Claims, 29 Drawing Sheets

(51) Int. Cl.
G01R 27/22 (2006.01)
G01L 19/08 (2006.01)
G01K 13/12 (2006.01)
G01N 30/00 (2006.01)

(56) References Cited

OTHER PUBLICATIONS

Anibas et al., "Transient or Steady-State? Using Vertical Temperature Profiles to Quantify Groundwater-Surface Water Exchange", Hydrological Processes vol. 23, 2009, United States, pp. 2165-2177.
Archie, "The Electrical Resistivity Log as an Aid In Determining Some Reservoir Characteristics", Petroleum Technology, Jan. 1942, United States, pp. 54-62.
Bouwer et al., "A Slug Test for Determining Hydraulic Conductivity of Unconfined Aquifers with Completely or Partially Penetrating Wells", Water Resources Research vol. 12, No. 3, Jun. 1976, United States, pp. 423-428.
Briggs et al., "Using High-Resolution Distributed Temperature Sensing to Quantify Spatial and Temporal Variability in Vertical Hyporheic Flux", Water Resources Research vol. 48, 2012, United States, 16 pages.
Chappell et al., "Comparison of Methodological Uncertainties within Permeability Measurements", Hydrological Processes vol. 21, 2007, United States, pp. 2504-2514.
Clauser et al., "Thermal Conductivity of Rocks and Minerals", Rock Physics and Phase Relations, 1995, United States, pp. 105-126.
Conant, "Delineating and Quantifying Ground Water Discharge Zones using Streambed Temperatures", Ground Water vol. 42, No. 2, Mar.-Apr. 2004, United States, pp. 243-257.
Constanta, "Heat as a Tracer to Determine Streambed Water Exchanges", Water Resources Research vol. 44, 2008, United States, 20 pages.
Demongodin et al., "Thermal Conductivity and Well Logs: A Case Study in the Paris Basin", Geophysical Journal International vol. 105, 1991, United Kingdom, pp. 675-691.
Fieckenstein et al., "Groundwater-Surface Water Interactions: New Methods and Models to Improve Understanding of Processes and Dynamics", Advances in Water Resources vol. 33, 2010, United Kingdom, pp. 1291-1295.
Freeze et al., "Groundwater", Prentice-Hall, 1979, United States, 606 pages.
Friedman, "Soil Properties Influencing Apparent Electrical Conductivity: A Review", Computers and Electronics in Agriculture vol. 46, 2005, Netherlands, pp. 45-70.
González-Pinzón et at, "A Field Comparison of Multiple Techniques to Quantify Groundwater-Surface-Water Interactions", Freshwater Science vol. 34, Mar. 2015, United States, pp. 139-160.
Gordon et al., "Automated Calculation of Vertical Pore-Water Flux from Field Temperature Time Series using the VFLUX Method and Computer Program, Journal of Hydrology vols. 420-421, 2012, Netherlands, pp. 142-158.
Gu et al., "An Iterative Ensemble Kalman Filter for Multiphase Fluid Flow Data Assimilation", Society of Petroleum Engineers SPE Journal vol. 12, Dec. 2007, United States, pp. 438-446.
Hammond et al., "Evaluating the Performance of Parallel Subsurface Simulators: An Illustrative Example with PFLOTRAN", Water Resources Research vol. 50, 2014, United States, pp. 208-228.
Hatch et al., "Quantifying Surface Water-Groundwater Interactions using Time Series Analysis of Streambed Thermal Records: Method Development", Water Resources Research vol. 42, 2006, United States, 14 pages.
Hoehn et al., "Radon in Groundwater: ATool to Assess Infiltration from Surface Waters to Aquifers", Water Resources Research vol. 25, 1989, United States, pp. 1795-1803.
Johns, et al., "A Two-Stage Ensemble Kalman Filter for Smooth Data Assimilation", Environmental and Ecological Statistics vol. 15, 2008, Netherlands, pp. 101-110.
Johnson et al., "Accurate Modelling and Inversion of Electrical Resistivity Data in the Presence of Metallic Infrastructure with Known Location and Dimension", Geophysical Journal International vol. 202, 2015, United Kingdom, pp. 1096-1108.
Johnson et al., "Improved Hydrogeophysical Characterization and Monitoring through Parallel Modeling and Inversion of Time-Domain Resistivity and Induced-Polarization Data", Geophysics vol. 75, No. 4, Jul.-Aug. 2010, United States, pp. WA27-WA41.
Johnson et al., "PFLOTRAN-E4D: A Parallel Open Source PFLOTRAN Module for Simulating Time-Lapse Electrical Resistivity Data", Computers & Geosciences vol. 99, 2017, United Kingdom, pp. 72-80.
Kalbus et al., "Measuring Methods for Groundwater—Surface Water Interactions: A Review", Hydrology and Earth System Sciences vol. 10, 2006, Germany, pp. 873-887.
Kamai et al., "Soil Water Flux Density Measurements Near 1 cm d-1 Using an Improved Heat Pulse Probe Design", Water Resources Research vol. 44, 2008, United States, 12 pages.
Keery et al., "Temporal and Spatial Variability of Groundwater-Surface Water Fluxes: Development and Application of an Analytical Method using Temperature Time Series", Journal of Hydrology vol. 336, 2007, Netherlands, pp. 1-16.
Kluitenberg et ai., "Improved Analysis of Heat Pulse Signals for Soil Water Flux Determination", Soil Science Society of America Journal vol. 71, No. 1, Jan.-Feb. 2007, United States, pp. 53-55.
Kruseman et al., "Analysis and Evaluation of Pumping Test Data", Second Edition (Completely Revised) Publication 47, International Institute for Land Reclamation and Improvement, 2000, Netherlands, 369 pages.
Lichtner et al., "A Massively Parallel Reactive Flow and Transport Model for Describing Surface and Subsurface Processes", PFLOTRAN User Manual, Jan. 20, 2015, United States, 195 pages.
Luce et al., "Solutions for the Diurnally Forced Advection-Diffusion Equation io Estimate Bulk Fluid Velocity and Diffusivity in Streambeds from Temperature Time Series", Water Resources Research vol. 49, 2013, United States, pp. 488-506.
McCallum et al., "A 1-D Analytical Method for Estimating Surface Water-Groundwater Interactions and Effective Thermal Diffusivity using Temperature Time Series", Water Resources Research vol. 48, 2012, United States, 8 pages.
Midttomme et al. "The Effect of Grain Size on Thermal Conductivity of Quartz Sands and Silts", Petroleum Geoscience vol. 4, 1998, United Kingdom, pp. 165-172.
Mori et al., "Estimation of Vadose Zone Water Flux from Multi-Functional Heat Pulse Probe Measurements", Soil Science Society of America Journal vol. 69, Apr. 11, 2005, United States, pp. 599-606.
Murdoch et al., "Factors Affecting the Performance of Conventional Seepage Meters", Water Resources Research vol. 39, Issue 6, Jun. 2003, United States, 10 pages.
Paulsen et al., "Development and Evaluation of an Ultrasonic Ground Water Seepage Meter", Ground Water vol. 39, No. 6, Nov.-Dec. 2001, United States, pp. 904-911.
Ren et al., "Determining Soil Water Flux and Pore Water Velocity by a Heat Pulse Technique", Soil Science Society of America Journal vol. 64, Mar.-Apr. 2000, United States, pp. 552-560.
Rosenberry et al., "Use of an Electromagnetic Seepage Meter to Investigate Temporal Variability in Lake Seepage", Ground Water vol. 42, No. 1, Jan.-Feb. 2004, United States, pp. 68-77.
Schmidt et al., "Characterization of Spatial Heterogeneity of Groundwater-Stream Water Interactions using Multiple Depth Streambed Temperature Measurements at the Reach Scale", Hydrology and Earth System Sciences vol. 10, 2006, Germany, pp. 849-859.
Schomberg et ai., "Simulating the Effects of Geologic Heterogeneity and Transient Boundary Conditions on Streambed Temperatures—Implications for Temperature-Based Water Flux Calculations", Advances In Water Resources vol. 33, 2010, United Kingdom, pp. 1309-1319.
Silliman et al., "Quantifying Downflow through Creek Sediments Using Temperature Time-Series—One-Dimensional Solution Incorporating Measured Surface-Temperature", Journal of Hydrology vol. 167, 1995, Netherlands, pp. 99-119.
Siripunvaraporn et al., "An Efficient Data-Subspace Inversion Method for 2-D Magnetoteliuric DataREBOCC Inversion for 2-D MT Data", Geophysics vol. 65, No. 3, May-Jun. 2000, United States, pp. 791-803.

(56) References Cited

OTHER PUBLICATIONS

Stallman, "Steady One-Dimensional Fluid Flow in a Semi-infinite Porous Medium with Sinusoidal Surface Temperature", Journal of Geophysical Research vol. 70, No. 12, Jun. 15, 1965, United States, pp. 2821-2827.

Stekiova et al., "3D Joint Hydrageophysical Inversion using Similarity Measures", Applied Mathematics and Computation, Nov. 24, 2017, Netherlands, 19 pages.

Taniguchi et al., "Evaluations of Groundwater Discharge Rates from Subsurface Temperature in Cockburn Sound, Western Australia", Biogeochemistry vol. 66, 2003, Netherlands, pp. 111-124.

Taniguchi et al., "Periodical Changes of Submarine Fluid Discharge from a Deep Seafloor, Suiyo Sea Mountain, Japan", Geophysical Research Letters vol. 30, No. 18, 2003, United States, 4 pages.

Vogt et al., "Fluctuations of Electrical Conductivity as a Natural Tracer for Bank Filtration in a Losing Stream", Advances in Water Resources vol. 33, 2010, United Kingdom, pp. 1296-1308.

Wang et al., "Investigating Spatial Variability of Vertical Water Fluxes Through the Streambed in Distinctive Stream Morphologies using Temperature and Head Data", Hydrogeology Journal vol. 25, Feb. 3, 2017, Germany, pp. 1283-1299.

Ward et al., "Characterizing Hyporheic Transport Processes—Interpretation of Electrical Geophysical Data in Coupled Stream—Hyporheic Zone Systems During Solute Tracer Studies", Advances in Water Resources vol. 33, 2010, United Kingdom, pp. 1320-1330.

Zhang et al., "Representative Hydraulic Conductivity of Hydrogeoiogic Units: Insights from an Experimental Stratigraphy", Journal of Hydrology vol. 339, 2007, Netherlands, pp. 65-78.

Campbell et al., "Probe for Measuring Soil Specific-Heat Using a Heat-Pulse Method", Soil Science Society of America Journal vol. 55, 1991, United States, pp. 291-293.

Cey et al., "Quantifying Groundwater Discharge to a Small Perennial Stream in Southern Ontario, Canada", Journal of Hydrology vol. 210, Issues 1-4, Sep. 1998, Netherlands, pp. 21-37.

Fritz et al., "Effect of Rapidly Changing River Stage on Uranium Flux through the Hyporheic Zone", Ground Water vol. 45, No. 6, 2007, United States, pp. 753-760.

Irvine et al., "Experimental Evaluation of the Applicability of Phase, Amplitude, and Combined Methods to Determine Water Flux and Thermal Diffusivity from Temperature Time Series using VFLUX 2", Journal of Hydrology vol. 531, Dec. 2015, Netherlands, pp. 728-737.

Krupa et al., "Krupaseep—The Next Generation Seepage Meter", Journal of Coastal Research vol. 25, 1998, United States, pp. 210-213.

Lewandowski et al., "A Heat Pulse Technique for the Determination of Small-Scale Flow Directions and Flow Velocities in the Streambed of Sand-Bed Streams", Hydrological Processes vol. 25, Issue 20, Feb. 2011, United States, pp. 3244-3255.

Schmidt et al., "Evaluation and Field-Scale Application of an Analytical Method to Quantify Groundwater Discharge using Mapped Streambed Temperatures", Journal of Hydrology vol. 347, Issues 3-4, Dec. 2007, Netherlands, pp. 292-307.

Shepherd, "Correlations of Permeability and Grain Size", Ground Water vol. 27, Issue 5, Sep. 1989, United States, pp. 633-638.

Surridge et al., "Evaluating the Quality of Hydraulic Conductivity Estimates from Piezometer Slug Tests in Peat", Hydrological Processes vol. 19, Issue 6, Mar. 18, 2005, United States, pp. 1227-1244.

Taniguchi et al. "Continuous Measurements of Groundwater Seepage Using an Automatic Seepage Meter", Ground Water vol. 31, Issue 4, Jul. 1993, United States, pp. 675-679.

Taniguchi et al., "Spatial and Temporal Distributions of Submarine Groundwater Discharge Rates Obtained from Various Types of Seepage Meters at a Site in the Northeastern Gulf of Mexico", Biogeochemistry vol. 66, Issue 1-2, Nov. 2003, Netherlands, pp. 35-53.

\* cited by examiner

US 11,714,078 B1

SYSTEMS AND METHODS FOR DETERMINING GROUND WATER-SURFACE WATER INTERACTIONS

CROSS REFERENCE TO RELATED APPLICATION

This application claims priority to and the benefit of U.S. Provisional Patent Application Ser. No. 62/683,944 which was filed on Jun. 12, 2018, the entirety of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

TECHNICAL FIELD

The present disclosure relates to environmental monitoring and more particularly to surface water and ground water monitoring.

BACKGROUND

Surface water flux across the soil-water boundary in ground water/surface water systems governs a number of ecological functions that are critical, for example, to riverine/lacustrine health and contaminant transport. However, traditional methods for monitoring provide limited, or partial information. For example, flux chambers provide the total mass flux but they do not provide any information on pore velocity or residence time. Vertical temperature arrays provide information on pore velocity and residence time, but do not provide information on total mass flux. Accordingly, improved probes and methods of sensing are needed.

SUMMARY OF THE DISCLOSURE

Systems for determining GW/SW interaction are provided. The systems can include: a sensing assembly comprising sensors for pressure, fluid conductivity, temperature, and transfer resistance; processing circuitry operatively coupled to the sensing assembly and configured to receive data from the sensing assembly and process the data to provide a GW/SW interaction, wherein the data includes pressure, fluid conductivity, temperature, transfer resistance data.

Methods for determining GW/SW interaction are provided. The methods can include: receiving real time data including pressure, fluid conductivity, temperature, and transfer resistance; from at least some of the data received simulating the SW/GW interaction; and fitting the real time data with the simulated data to provide actual SW/GW interaction.

DESCRIPTION

Figure 1:
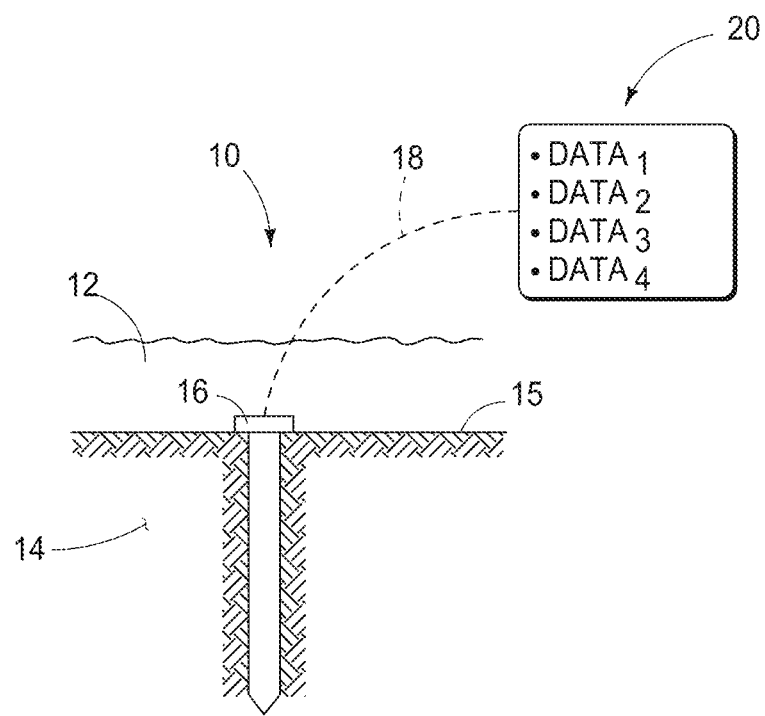
FIG. 1 depicts a system according to an embodiment of the disclosure.

Disclosed are probes and methods for sensing parameters at an interface between groundwater and surface water. Groundwater/surface water flux monitoring approaches that estimate either transient pore fluid velocity or mass flux rate at the surface water/groundwater interface are limited in usefulness. Described herein are multi-sensor probes and methods for sensing that continuously monitors the spatial (e.g., vertical) distribution of pore fluid conductivity, temperature, pressure, and bulk electrical conductivity. Combined with fluid conductivity, bulk electrical conductivity can be used to estimate the vertical distribution of porosity, which links pore fluid velocity to mass flux. We developed the capability to simulate all time-series data from the probe using PFLOTRAN-E4D, and a joint Occam's inversion for estimating the simplest vertical distribution of porosity, permeability, and dispersivity that honor the data. We have also developed a companion stochastic analysis to investigate uncertainty in parameter estimates and corresponding flux rates. Once parameters are estimated, transient pore fluid velocity and mass flux can be monitored using only the pressure sensors located at the top and bottom of the sensor probe to determine dynamic pore fluid velocity and mass flux.

The systems and methods of the present disclosure were developed to address capability limitations of current sensing techniques to measure the dynamic flux of water across the GW/SW boundary. Surface water flux across the soil-water boundary in ground water/surface water system governs a number of ecological functions that are critical to riverine/lacustrine health and contaminant transport. There are currently two predominant methods to monitor surface water flux; flux chambers and vertical temperature arrays. Flux chambers provide the total mass flux but they do not provide any information on pore velocity or residence time. Vertical temperature arrays provide information on pore velocity and residence time, but do not provide information on total mass flux. The systems and/or methods of the present disclosure can be used to monitor dynamic (i.e. time varying) pore fluid velocity, residence time, and total mass flux, with the added benefits of estimating the in situ porosity and hydraulic conductivity of the sediment adjacent to the probe.

Embodiments of the present disclosure can combine electrical geophysical measurements (collected using ring electrodes on the outer shell of the sensing assembly) with traditional pressure, temperature, and fluid conductivity measurements (collected using sensors installed on the inner spine, inside of the shell of the sensing assembly). The geophysical measurements are sensitive to porosity, which provides the parameter necessary to convert pore fluid velocity to mass flux.

The systems and methods of the present disclosure can utilize a thermal contrast between surface water and groundwater as well as contrasts in fluid electrical conductivity between surface water and groundwater. Temperature based flux measurements only provide pore fluid velocity, and not mass flux, and assume steady state pressure boundary conditions. The systems and methods of the present disclosure can provide both pore fluid velocity and mass flux under dynamic pressure boundary conditions. Temperature based flux measurements do not provide information about vertical sediment structure. The systems and methods of the present disclosure can provide the vertical distribution of sediment porosity and permeability.

The systems and methods of the present disclosure can use geophysical measurements to estimate in situ sediment porosity and permeability which allows for the conversion boundary pressure measurements to Darcy's flux and pore velocity. These natural tracer flux measurements can then used to calibrate differential pressure to use the Darcian approach to measure dynamic flux even when natural tracers cannot be used. In most cases where there is a contrast in fluid conductivity between GW and SW these measurements can be used to determine if the flux of water is truly GW, SW or a mix of GW and SW which can all occur under dynamic stage conditions.

The sensing assembly can include a vertical array of sensors (electrodes, thermistors, fluid specific conductance probes, and pressure sensors) that are installed into the sediment at the lower boundary of a water body (e.g. stream, river, lake or tidal zone). The sensors can be deployed on a linear, non-metallic conduit (approximately 2-5 cm in diameter and 50-300 cm long). The conduit can include a series of ring electrodes that can be used to monitor the bulk electrical conductivity time-series of the sediment along the longitudinal axis. A conduit can also be equipped with miniature sensors that monitor pressure, temperature, and fluid conductivity along the vertical axis of the tool.

Referring first to FIG. 1, a sensing assembly 16 is shown within a GW/SW environment 10. As depicted ground water exists in earth 14 and below surface water 12 and GW/SW barrier 15. Sensing assembly 16 can include sensors configured to sense changes in multiple physical parameters 20. These physical parameters can include pressure, fluid conductivity, temperature, and transfer resistance. Sets of these sensors can be provided for each of the physical parameters. These sets of sensors can be spaced apart predetermined distances and these distances can be associated with a depth below the GW/SW barrier. Accordingly, the systems and methods can be used to determine vertical GW/SW interactions which in turn can be used to determine porosity, permeability and/or dynamic flow processes.

Figure 2A:
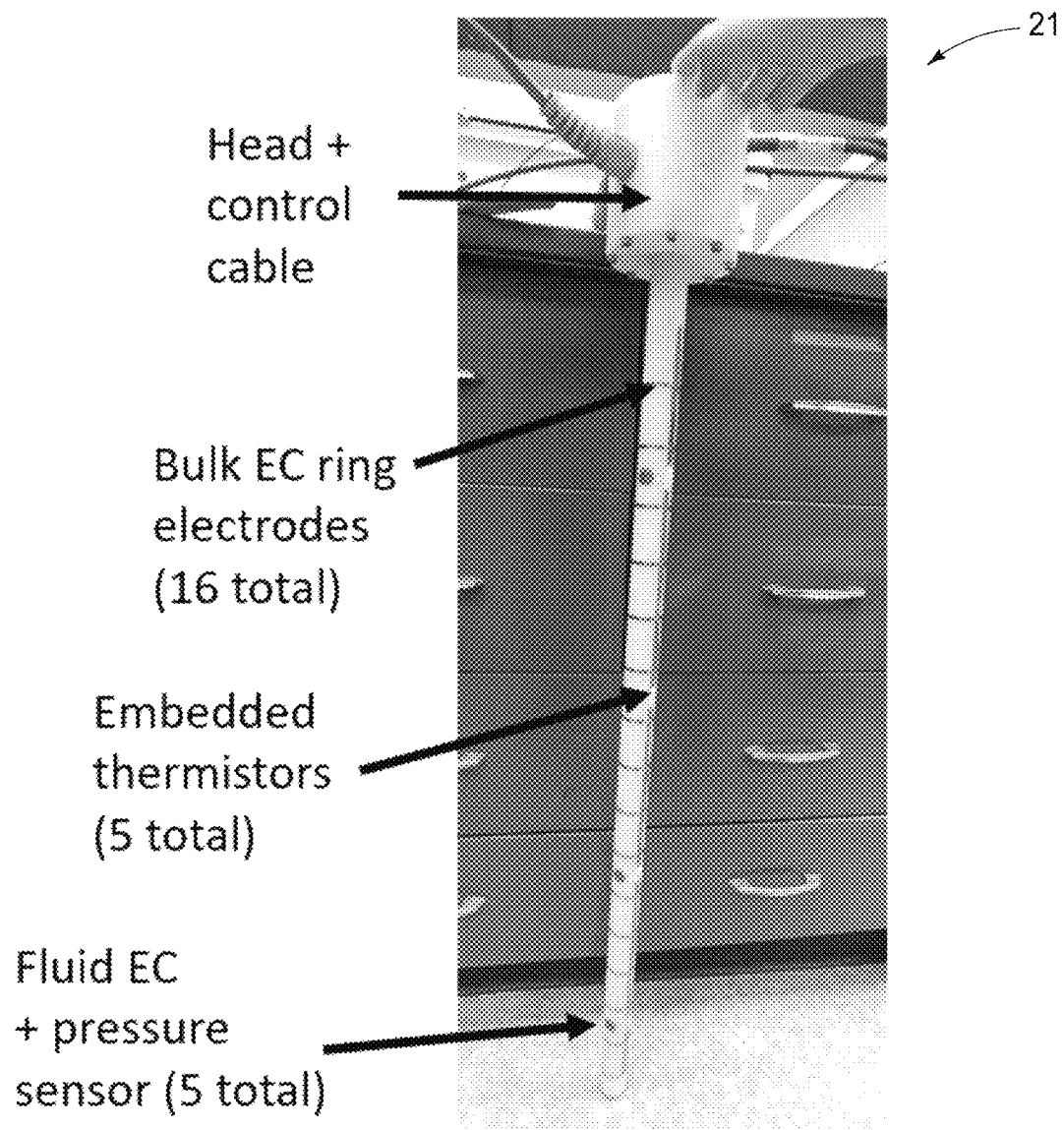
FIG. 2A is a depiction of a sensing assembly according to an embodiment of the disclosure.
Figure 2B:
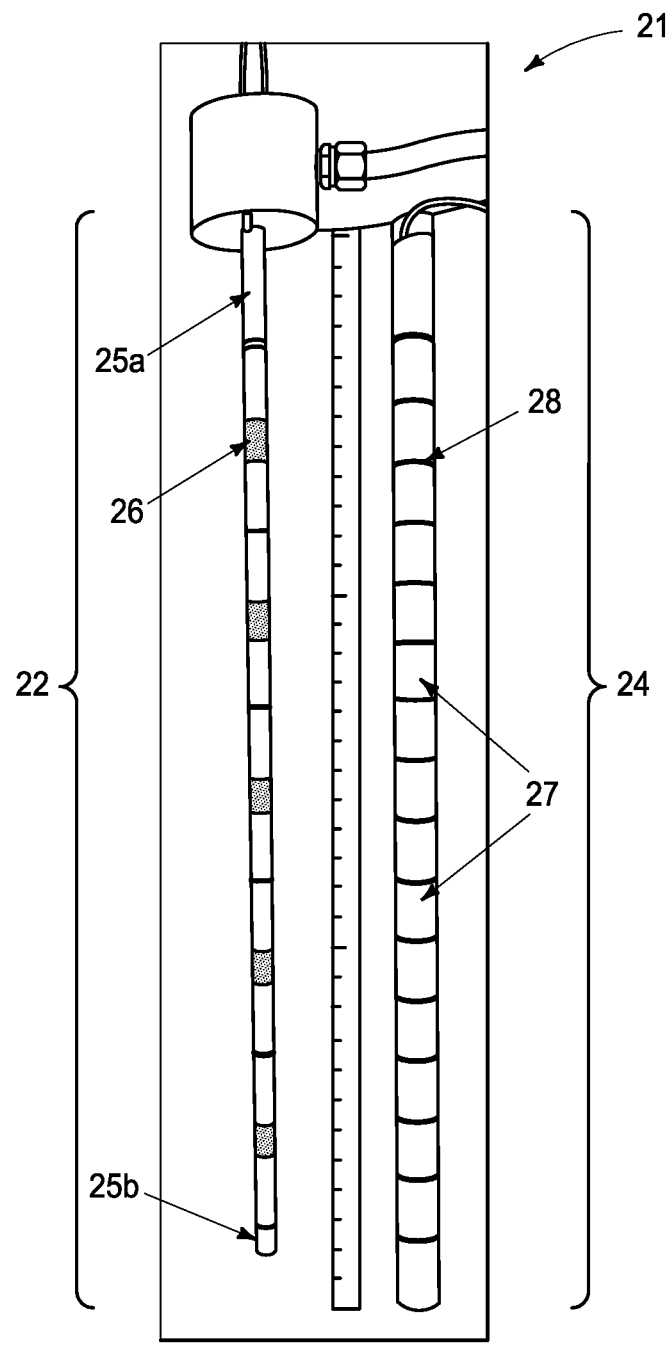
FIG. 2B is a depiction of another sensing assembly according to an embodiment of the disclosure.
Figure 3:
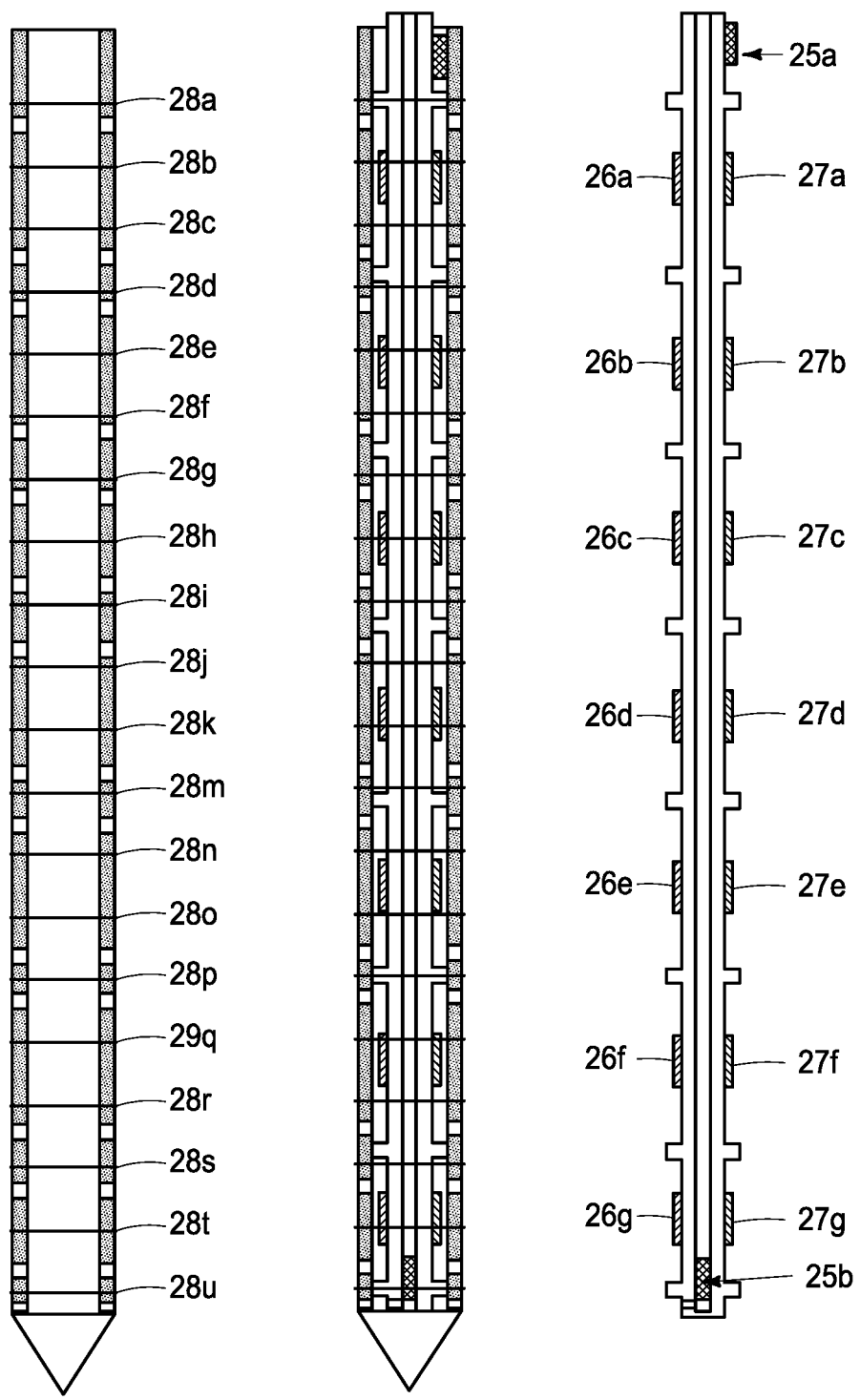
FIG. 3 is a depiction of components of the sensing assembly of FIG. 2B according to an embodiment of the disclosure.

In accordance with at least one embodiment of the disclosure and with reference to FIGS. 2A, 2B, and 3, sensing assemblies are depicted that include both inner 22 and outer rods 24 of the flux tool. Inner rod 22 can include upper 25a and lower 25b pressure sensors and fluid conductivity sensors 26. Pore fluid within the groundwater may accesses the fluid conductivity sensors via ports installed in the outer rod. Outer rod 24 can include embedded thermistors 27 (temperature sensors) and bulk conductivity electrodes 28. Referring to FIG. 3, sets of these sensors can be provided along the length of the sensing assembly a predetermined distance from one another; for example, pressure sensors 25a-b, fluid conductivity sensors 26a-g, temperature sensors 27a-g, and bulk conductivity electrodes 28a-u.

In accordance with example implementations, the rod can be installed vertically into a river-bottom or other groundwater/surface water interface. Data from each sensor can then be collected.

Accordingly, sensors can record the pressure, fluid conductivity, and temperature time-series along the length rod, including the upper and lower boundary conditions. The ring electrodes can be used to make transfer resistance measurements in a 4-electrode configuration, for example. The thermistors (temperature sensors) can be calibrated to operate between 5-30 degrees C. The fluid conductivity cells can use four-electrodes built into a flexible circuit board that can be installed around the circumference of the inner rod (see FIGS. 2-3). When the inner rod is inserted into the outer rod, the O-rings on the inner rod seal to the inside surface of the outer rod, thereby bounding the electrical field within the measurement chamber. Vertical slits on the outer rod allow water to pass through the sensor. These slits can be located at the top and bottom of the sensor cell and were 1 cm long and 0.5 mm wide and can be located 10 cm apart from top to bottom of the cell and also located on opposite sides of the sensing assembly. The cell constant for the fluid conductivity sensors can be calibrated using 4 sodium chloride solutions ranging from 0.0044 to 0.298 S/m. Nylon tubes can be used between the pressure ports and the differential pressure transducers located in the sensing assembly head.

Figure 4:
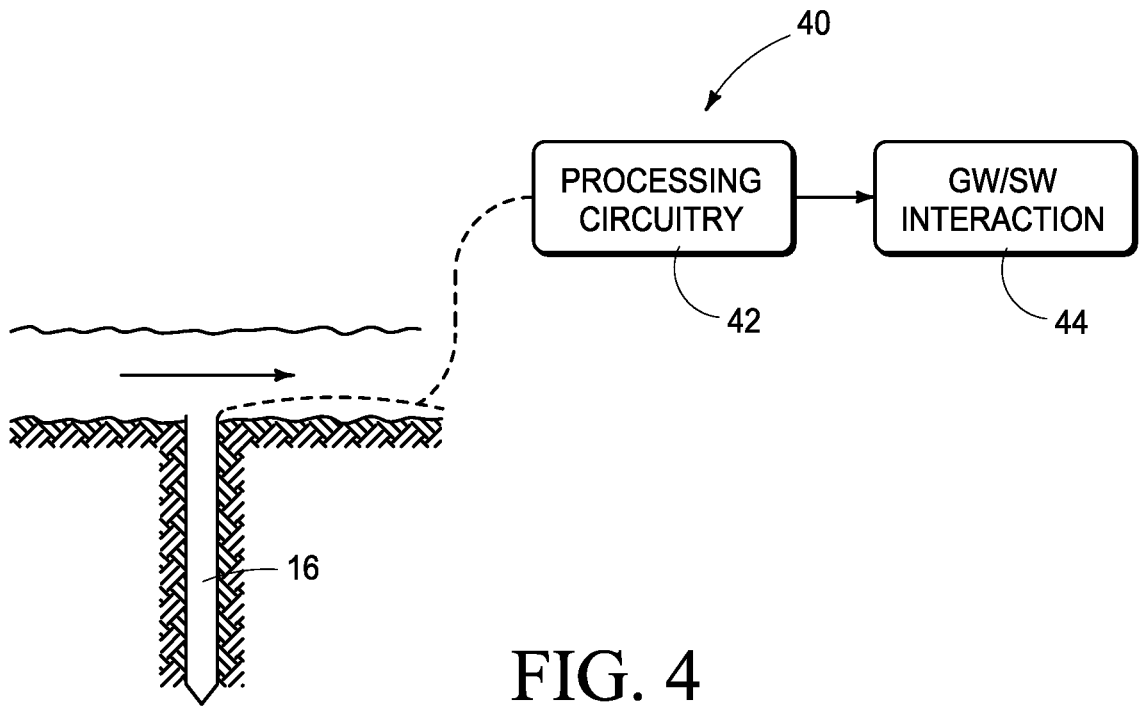
FIG. 4 is a system for determining SW/GW interactions according to an embodiment of the disclosure.

Referring to FIG. 4, this data can be processed to determine GW/SW interaction. In accordance with example implementations, some fundamentals of SW/GW relationships are relied upon. For example, Porosity can be estimated using Archie's law (Archie, 1942). For a saturated system, Archie's law relates the bulk conductivity ($\sigma_{bulk}$)t to the fluid conductivity ($\sigma_{fluid}$) using the formation factor (F) seen in Equation 1.

$$\sigma_{Bulk} = \sigma_{fluid} \quad (1)$$

$\sigma_{Bulk}$ cannot be measured directly, but transfer resistance measurements can be inverted to obtain or $\sigma_{Bulk}$.

Furthermore, F is a function of porosity (n) and the cementation exponent (m) by the relationship seen in Equation 2.

$$F = n^{-m} \quad (2)$$

For granular media, particle shape is a major factor affecting m. For spherical particles m is about 1.35, but can be as high as 1.65 for prismatic and angular shaped particles.

Pore water velocity can be estimated using time series data from different locations along the flow path of a conservative tracer. In most GW-SW interaction zones, electrical conductivity (EC) can be used as a natural conservative tracer due to the differences between the electrical conductivity of GW and SW. Freshwater lakes and streams have specific conductance values ranging from 2-100 µS/cm, GW, wetlands and bogs generally range from 50-50,000 µS/cm, and ocean water is generally around 50,000 µS/cm. According to EPA, river water in the United States ranges in conductivity from 50-1500 µS/cm.

For a 3-D system, bulk electrical conductivity of the subsurface can be imaged by inverting time lapse electrical resistivity tomography (ERT) measurements. This provides spatial and temporal conductivity estimates at locations where the system is sensitive to ERT measurements. This time lapse data can then be used to identify breakthroughs of a conductive tracer passing through the system. Transfer resistance values were directly used to measure breakthroughs of either GW or SW by using their difference in electrical conductivity as a natural tracer.

For both gaining and losing steams, the temperature profile can be used as a natural tracer to estimate pore water velocity. This can be utilized wherein there is a temperature contrast between GW and SW, which is generally true for streams and rivers that have diurnal and/or seasonal temperature swings. To date, no analytical solution was found to use temperature as a natural tracer in dynamic systems with unpredictable pressure boundary conditions, thus PFLOTRAN, a parallel multi-physics code used to simulate reactive flow and transport through porous materials, was used to predict temperature at 4 of the 5 thermistor locations for comparison with observed data.

Water passing through porous media experiences a resistance to flow. This resistance to flow is quantified using Darcy's law that relates the specific discharge also known as Darcy's flux (q) to the hydraulic gradient $$\left(\frac{dh}{dl}\right)$$

using the hydraulic conductivity (K), which is considered a property of the porous media (see Equation 3).

$$q = -K\left(\frac{dh}{dl}\right) \quad (3)$$

For a gaining or loosing stream, quasi steady state Darcy's flux can be estimated using the temperature profile below the river bed. The temperature amplitude and phase shift at different depths driven by diurnal temperature fluctuations of surface water to calculate a vertical flux value can be used for steady state Darcy's flux. This approach may be applied easily in the field. The analytical solution to a one-dimensional steady-state heat advection-diffusion equation can be used to calculate the flux values as applied in Schmidt et al. (2007) (see Equation 4).

$$q_Z = -\frac{K_{fs}}{(\rho_f C_f Z)} \ln(T_Z - T_L)/(T_0 - T_L) \quad (4)$$

where, $T_Z$ is the streambed temperature at depth z (° C.), $T_L$ is the lower temperature boundary (° C.), $T_0$ is the temperature at Z=0 (° C.), $\rho_f C_f$ is the volumetric heat capacity of the fluid (J m$^{-3}$K$^{-1}$), and $K_{fs}$ is the thermal conductivity of the solid-fluid system (J s$^{-1}$ m$^{-1}$ K$^{-1}$). $K_{fs}$ is calculated using the geometric mean of the thermal conductivity of sand $K_s$ and the thermal conductivity of fluid $K_f$ as can be seen in Equation 5, where n is the porosity.

$$K_{fs} = K_s^{(1-n)} K_f^n \quad (5)$$

$K_s$ is assumed to be between 7.7 to 8.4 J s$^{-1}$ m$^{-1}$ K$^{-1}$ which is the thermal conductivity of solid quartz. However, the thermal conductivity of saturated sand was best fit to 2.86 J s$^{-1}$ m$^{-1}$K$^{-1}$ where the relationship of the average grain size $d_m$ (micron) to the thermal conductivity of solid-fluid system was calculated using Equation 6.

$$K_s = 0.215 \ln d_m + 1.93 \quad (6)$$

Referring next to FIG. 4, a system 40 is depicted that includes sensing assembly 16 operationally coupled to processing circuitry 42 which is configured to provide GW/SW interaction data 44. In accordance with example implementations, processing circuitry 42 can be operationally coupled to sensing assembly 16 via cables, wirelessly, and/or integrated as part of sensing assembly 16.

Figure 5:
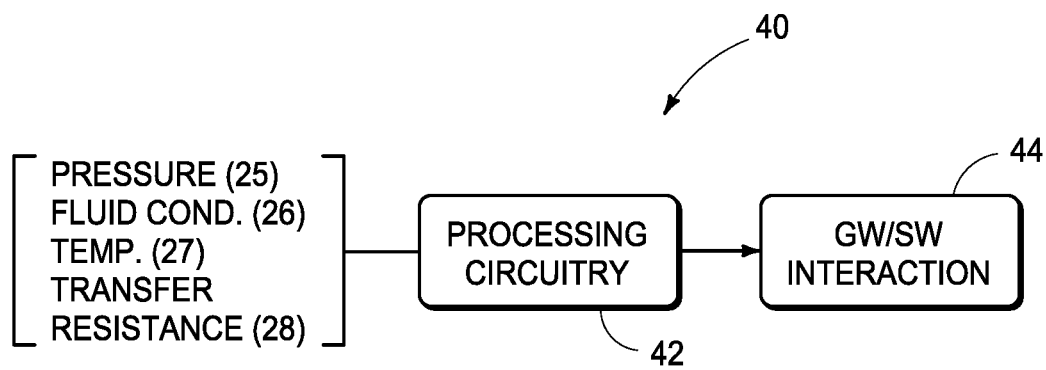
FIG. 5. is another configuration of a system for determining SW/GW interactions according to an embodiment of the disclosure.

Referring next to FIG. 5, system 40 is shown receiving pressure (25), fluid conductivity (26), temperature (27), and transfer resistance (28) data from the sensing assembly. Each of these parameters can be associated with a time and/or a depth below the SW/GW barrier.

Figure 6:
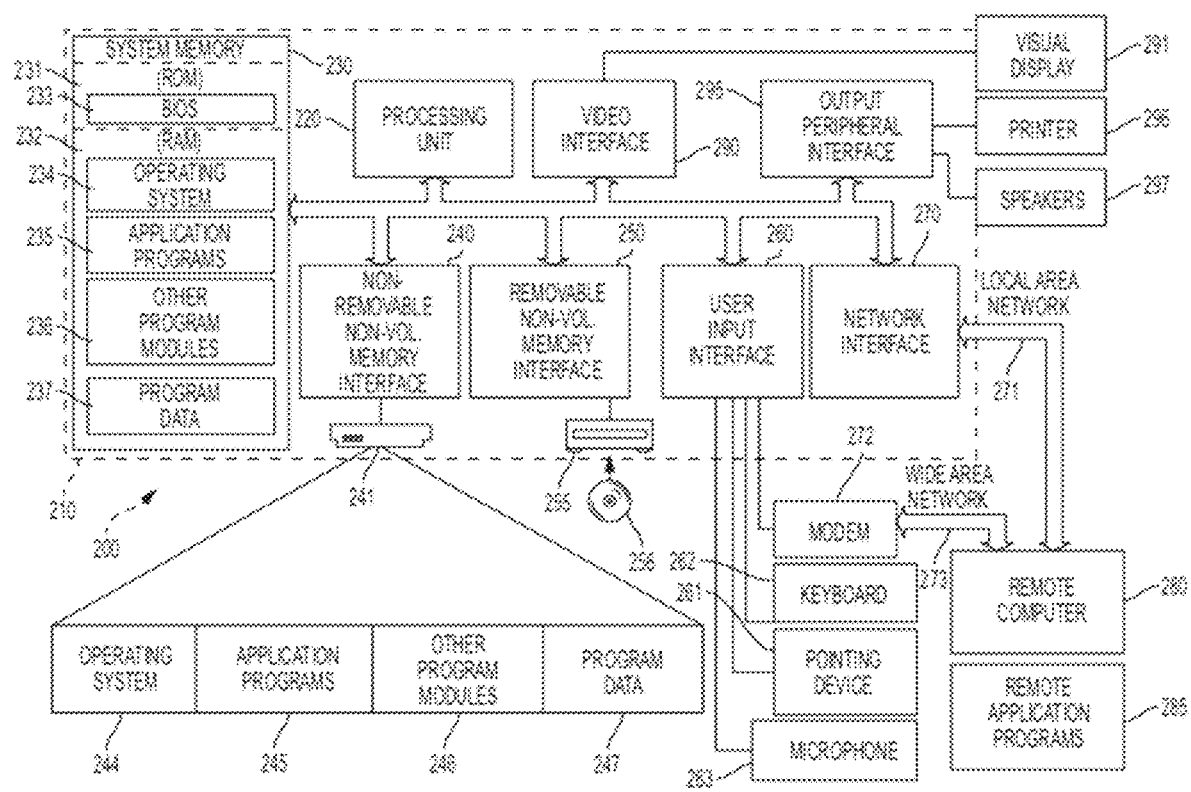
FIG. 6 is a portion of a system according to an embodiment of the disclosure.

Referring next to FIG. 6, and example embodiment of processing circuitry 42 is shown with which the sensing assembly can operationally interfaced. In one example, a computing environment such as shown in FIG. 6 can be used to log data from the sensing assembly, to analyze data from the sensing assembly and/or to perform simulations based on sensing assembly data, as well as fit real time and/or recorded/stored data with simulated data. In accordance with example implementations, the processing circuitry is configured to provide simulated SW/GW interaction and real time SW/GW interaction, and process those interactions to fit the simulated SW/GW interaction with the real time SW/GW interaction to provide a modified SW/GW interaction. The modified SW/GW interaction can be provided continually in an iterative process.

For example, processing circuitry 42 can be used to simulate all time-series data from the sensing assembly using PFLOTRAN-E4D, and a joint Occam's inversion for estimating the vertical distribution of porosity, permeability, and dispersivity from the data received. Furthermore, a companion stochastic analysis can be performed with the processing circuitry to determine uncertainty in parameter estimates and corresponding flux rates. Once parameters are estimated, transient pore fluid velocity and mass flux can be monitored using only the pressure sensors located at the top and bottom of the sensing assembly.

The time series data can be jointly inverted as described below to estimate the vertical distribution of porosity and permeability, pore fluid velocity and vertical mass flux time-series.

The combined monitoring data are processed using analysis techniques developed specifically for the systems and methods of the present disclosure. The techniques involving the use of U.S. Pat. No. 9,772,423 may be utilized, the entirety of which is incorporated herein by reference.

With reference to FIG. 6, an example system for implementing some embodiments includes a general-purpose computing device in the form of a computer 210. Components of computer 210 may include, but are not limited to, a processing unit 220 (which is not limited to CPUs, but can comprise GPUs), a system memory 230, and a system bus 221 that couples various system components including the system memory to the processing unit 220. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro ChannelArchitecture (MCA) bus, Enhanced ISA (EISA) bus, Video Electronics Standards Association (VESA) local bus, and Peripheral Component Interconnect (PCI) bus also known as Mezzanine bus. Memory and programs described herein be deployed in corresponding portions of FIG. 6.

Computer 210 typically includes a variety of computer readable media. Computer readable media can be any available media that can be accessed by computer 210 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, sash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 210. Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 230 includes computer storage media in the form of volatile and/or nonvolatile memory such as read only memory (ROM) 231 and random-access memory (RAM) 232. A basic input/output system 233 (BIOS), containing the basic routines that help to transfer information between elements within computer 210, such as during startup, is typically stored in ROM 231. RAM 232 typically contains data and/or program modules that are immediately accessible to and/or presently being operated on by processing unit 220. By way of example, and not limitation, FIG. 6 illustrates operating system 234, application programs 235, other program modules 236, and program data 237.

The computer 210 may also include other removable/nonremovable volatile/nonvolatile computer storage media. By way of example only, FIG. 6 illustrates a hard disk drive 241 that reads from or writes to non-removable, nonvolatile magnetic media, and an optical disk drive 255 that reads from or writes to a removable, nonvolatile optical disk 256 such as a CD ROM or other optical media. Other removable/non-removable, volatile/nonvolatile computer storage media that can be used in the exemplary operating environment include, but are not limited to, magnetic tape cassettes, sash memory cards, digital versatile disks, digital video tape, solid state RAM, solid state ROM, and the like. The hard disk drive 241 is typically connected to the system bus 221 through a nonremovable memory interface such as interface 240, and optical disk drive 255 are typically connected to the system bus 221 by a removable memory interface, such as interface 250.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specisc Integrated Circuits (ASICs), Program-specisc Standard Products (ASSPs), System-on-a-chip systems (SOCs), Complex Programmable Logic Devices (CPLDs), etc.

The drives and their associated computer storage media discussed above and illustrated in FIG. 6, provide storage of computer readable instructions, data structures, program modules and other data for the computer 210. In FIG. 6, for example, hard disk drive 241 is illustrated as storing operating system 244, application programs 245, other program modules 246, and program data 247. Note that these components can either be the same as or different from operating system 234, application programs 235, other program modules 236, and program data 237. Operating system 244, application programs 245, other program modules 246, and program data 247 are given different numbers here to illustrate that, at a minimum, they are different copies.

A user may enter commands and information into the computer 210 through input devices such as a keyboard 262, a microphone 263, and a pointing device 261, such as a mouse, trackball or touch pad. Other input devices (not shown) may include a joystick, game pad, satellite dish, scanner, or the like. These and other input devices are often connected to the processing unit 220 through a user input interface 260 that is coupled to the system bus, but may be connected by other interface and bus structures, such as a parallel port, game port or a universal serial bus (USB). A visual display 291 or other type of display device is also connected to the system bus 221 via an interface, such as a video interface 290. Video interface 290 can comprise a graphics card having a GPU. The GPU be used for computations. In addition to the monitor, computers may also include other peripheral output devices such as speakers 297 and printer 296, which may be connected through an output peripheral interface 295.

The computer 210 is operated in a networked environment using logical connections to one or more remote computers, such as a remote computer 280. The remote computer 280 may be a personal computer, a hand-held device, a server, a router, a network PC, a peer device or other common network node, and typically includes many or all of the elements described above relative to the computer 210. The logical connections depicted in FIG. 6 include a local area network (LAN) 271 and a wide area network (WAN) 273, but may also include other networks. Such networking environments are commonplace in offices, enterprise-wide computer networks, intranets and the Internet.

When used in a LAN networking environment, the computer 210 is connected to the LAN 271 through a network interface or adapter 270. When used in a WAN networking environment, the computer 210 typically includes a modem 272 or other means for establishing communications over the WAN 273, such as the Internet. The modem 272, which may be internal or external, may be connected to the system bus 221 via the user input interface 260, or other appropriate mechanism. In a networked environment, program modules depicted relative to the computer 210, or portions thereof, may be stored in the remote memory storage device. By way of example, and not limitation, FIG. 6 illustrates remote application programs 285 as residing on remote computer 280. It will be appreciated that the network connections shown are exemplary and other means of establishing a communications link between the computers may be used.

Figure 7:
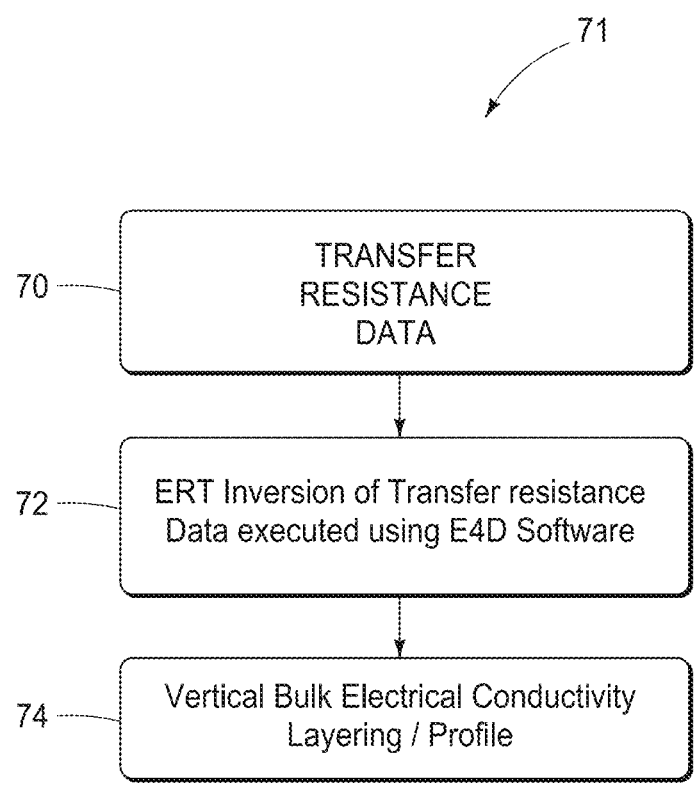
FIG. 7 is a portion of methods for determining SW/GW interactions according to an embodiment of the disclosure.

Referring next to FIG. 7, an example process 71 used by processing circuitry 42 for processing transfer resistance data is shown. Accordingly transfer resistance data is received by processing circuitry 42 at 70. Using processing circuitry 42, at 72 an ERT inversion of the data of 70 is executed using E4D Software. (E4D software is available from the Pacific Northwest National Laboratory).

E4D is a parallel ERT forward modeling and inversion code. Data are collected along the sensing assembly using a four-electrode Wenner-alpha configuration, whereby current is injected between two outer source and a sink electrodes, and the resulting electrical potential is measured between a positive and negative potential electrode, each lying between the current electrodes. Measurements proceed down the sensing assembly using 4 adjacent electrodes in sequence to produce thirteen measurements at a given time step.

The direct-current electrical potential arising from a given current source is given by the Poisson equation (7)

$$\nabla \cdot \sigma_b \nabla \phi = -\nabla \cdot J, \quad (7)$$

with bulk conductivity $\sigma_b$, electrical potential $\phi$, and source current density J. Given $\sigma_b$, J, and appropriate boundary conditions, the objective of the forward modeling is to solve Equation (7) for $\phi$, which is measured during an ERT experiment. Simulation of the voltage across potential electrodes normalized by the injected current, namely the transfer resistance, is summarized as $$R = A_e(\sigma_b), \quad (8)$$

with transfer resistance R, and ERT forward operator $A_e$. In time-lapse ERT surveys, both the transfer resistance and bulk conductivity are functions of time. E4D solves Equation (7) using the finite element method on an unstructured tetrahedral mesh. The ring electrodes and rod of the flux tool are modeled in true dimension using the non-point source electrode modeling method described by Johnson and Wellman [2015]. At 74, using processing circuitry 42, a vertical bulk electrical conductivity profile is provided.

Figure 8:
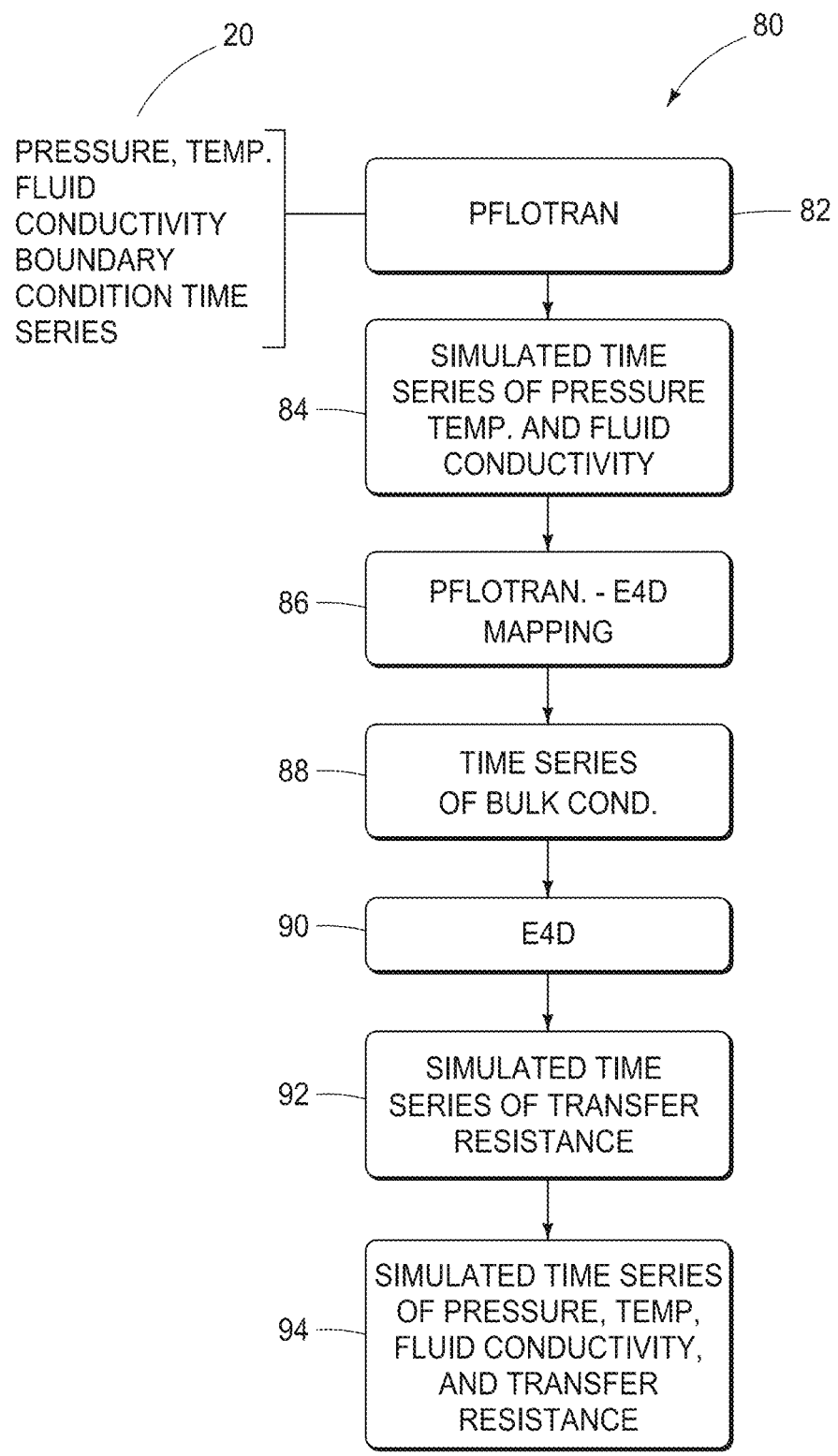
FIG. 8 is another portion of methods for determining SW/GW interactions according to an embodiment of the disclosure.

Referring next to FIG. 8, an example process used by processing circuitry 42 for processing pressure, temperature, and fluid conductivity boundary data over time is shown. Accordingly, the data is received by processing circuitry 42 and PFLOTRAN (Open Source) simulation is performed at 82 to prepare a simulated time series of pressure temperature and fluid conductivity from data 20.

PFLOTRAN is a parallel multi-physics code that simulates reactive flow and transport in porous materials. PFLOTRAN simulates liquid phase flow and solute transport based on the following conservation equations of mass, energy, and solute transport $$\frac{\partial}{\partial t}(\varphi s \rho) + \nabla \cdot (\rho q) = 0, \quad (9)$$

$$\frac{\partial}{\partial t}(\varphi s \rho U + (1-\varphi)\rho_r c_r T) + \nabla \cdot (\rho q H - \kappa \nabla T) = 0, \quad (10)$$

$$\frac{\partial}{\partial t}(\varphi s C) + \nabla \cdot (q - \varphi s D \nabla)C = 0, \quad (11)$$

with porosity $\varphi$, saturation s, water density $\rho$, Darcy velocity q, fluid internal energy U, rock density $\rho_r$, rock heat capacity $c_r$, water temperature T, fluid enthalpy H, bulk thermal conductivity $\kappa$, solution concentration C, and dispersion coefficient D. The Darcy velocity (or Darcy flux) q is given by $$q = -\frac{k}{\mu}\nabla(P - \rho g z), \quad (12)$$

with permeability k, viscosity $\mu$, water pressure P, acceleration of gravity g, vertical position z. The Darcy velocity q gives discharge per unit area, which is not the actual fluid speed traveling through the porous medium. Instead, the actual pore fluid velocity (or seepage velocity) v is computed as $$v = -\frac{q}{\varphi}. \quad (13)$$

For SW/GW interactions in this paper, we assume incompressible flows (i.e. water density is a known constant value) and the following relations $$U = H - \frac{P}{\rho} \quad (14)$$

$$dH = c_p dT + V(1 - \alpha T)dP \quad (15)$$

with water heat capacity $c_p$, system volume V, and thermal expansion coefficient $\alpha$. Equation (14) is obtained from an equation of state for pure water; Equation (15) describes the dependency of enthalpy as a function of temperature and pressure.

There can be 6 scalar unknowns (water pressure P, 3 components of Darcy velocity q, water temperature T, and solute concentration C), which can be obtained by solving 6 scalar equations (conservation of mass, 3 components of Darcy' Law, conservation of energy, and conservation of solute transport). PFLOTRAN employs backward Euler time discretization and the Newton-Raphson method to solve for flow, heat, and transport state variables over time. In the 1D mass flux monitoring and inversion at the GW-SW interface, the unknown model parameters are the vertically distributed permeability and porosity. Given the boundary and initial conditions of pressure, temperature, and fluid conductivity at the top and bottom of the system, the hydrogeologic modeling of dynamic temperature and fluid conductivity can be summarized as $$(T, \sigma_w) = A_h(k, \varphi), \tag{16}$$

with fluid conductivity $\sigma_w$, and hydrogeologic forward operator $A_h$. The hydrogeologic forward operator in Equation (16) represents the process of solving the partial differential equations (9) to (11) with the relation Equation (12) and appropriate boundary and initial conditions.

At 86 a combination of PFLOTRAN and E4D mapping is performed using processing circuitry 42. PFLOTRAN-E4D is a parallel ERT module for PFLOTRAN to simulate the evolution of subsurface resistivity and corresponding transfer resistance measurements arising from a particular process [Johnson et al., 2017]. The code receives the evolution of subsurface states from PFLOTRAN, converts those states to bulk electrical conductivity, and simulates a specified set of transfer resistance data.

We use Archie's Law [Archie, 1942] to describe the petrophysical relationship between the fluid conductivity and bulk conductivity as $$\sigma_b = \frac{1}{a} \varphi^m s^n \sigma_w, \tag{17}$$

with tortuosity factor a, cementation exponent m, and saturation exponent n. The formation factor F is defined as the ratio of the fluid conductivity to the bulk conductivity of saturated sediments (s=1)

$$F = \frac{a}{\varphi^m} = \frac{\sigma_w}{(\sigma_b)_{s=1}}. \tag{18}$$

With predetermined parameters of a, m, and n, the petrophysical transform in Equation (17) can be denoted by $$\sigma_b = A_p(\sigma_w, \varphi). \tag{19}$$

For the saturated applications described herein, s=1 so s and n do not contribute to solution uncertainty. Conversely, a and m contribute to uncertainty in the inversion solution as described in the forthcoming discussion. The hydrogeophysical modeling of the data collected at the SW/GW interface can be represented as $$(T, \sigma_w, R) = A(k, \varphi). \tag{20}$$

where A denotes the hydrogeophysical forward operator that integrates operators $A_h$, $A_p$, and $A_e$.

$$A(k, \varphi) = (A_h(k, \varphi), A_p(\sigma_w, \varphi), A_e(\sigma_b)) \tag{21}$$

There can be three steps in the hydrogeophysical forward modeling, (1) PFLOTRAN simulation of temperature and fluid conductivity, given the boundary and initial conditions of pressure, temperature, and fluid conductivity measured at the top and bottom of the flux tool (Eq. 13); (2) computation of bulk conductivity using Archie's Law after mapping porosity and fluid conductivity from PFLOTRAN to the E4D mesh (Eq. 8); and (3) E4D simulation of time-lapse transfer resistance data (Eq. 9).

We further simulate the hydrogeophysical data (i.e. temperature, fluid conductivity, and transfer resistance) at $N_r^{sum}$ locations (total number of thermistors, fluid conductivity sensors, and Wenner-alpha arrays, sensors used for boundary conditions excluded) and $N_t$ time steps. Using discrete data and model parameters, the 1D hydrogeophysical modeling can be written in matrix form as $$d = A(m), \tag{22}$$

where $d = [T^T, \sigma_w^T, R^T]^T$ denotes the $N_d$ length data vector, $N_d = N_r^{sum} N_t$, A denotes the discretized hydrogeophysical operator A in Eq. (21), and $m = [k^T, \varphi^T]^T$ denotes the $N_m$ length model vector of layered permeability and porosity, $N_m = 2N_l$. Superscript T indicates vector transpose.

At 88, time series of bulk conductivity is received and processed using E4D to prepare a time series of transfer resistance data at 92. At 94, simulated time series data for pressure, temperature, fluid conductivity, and transfer resistance is provided.

Figure 9:
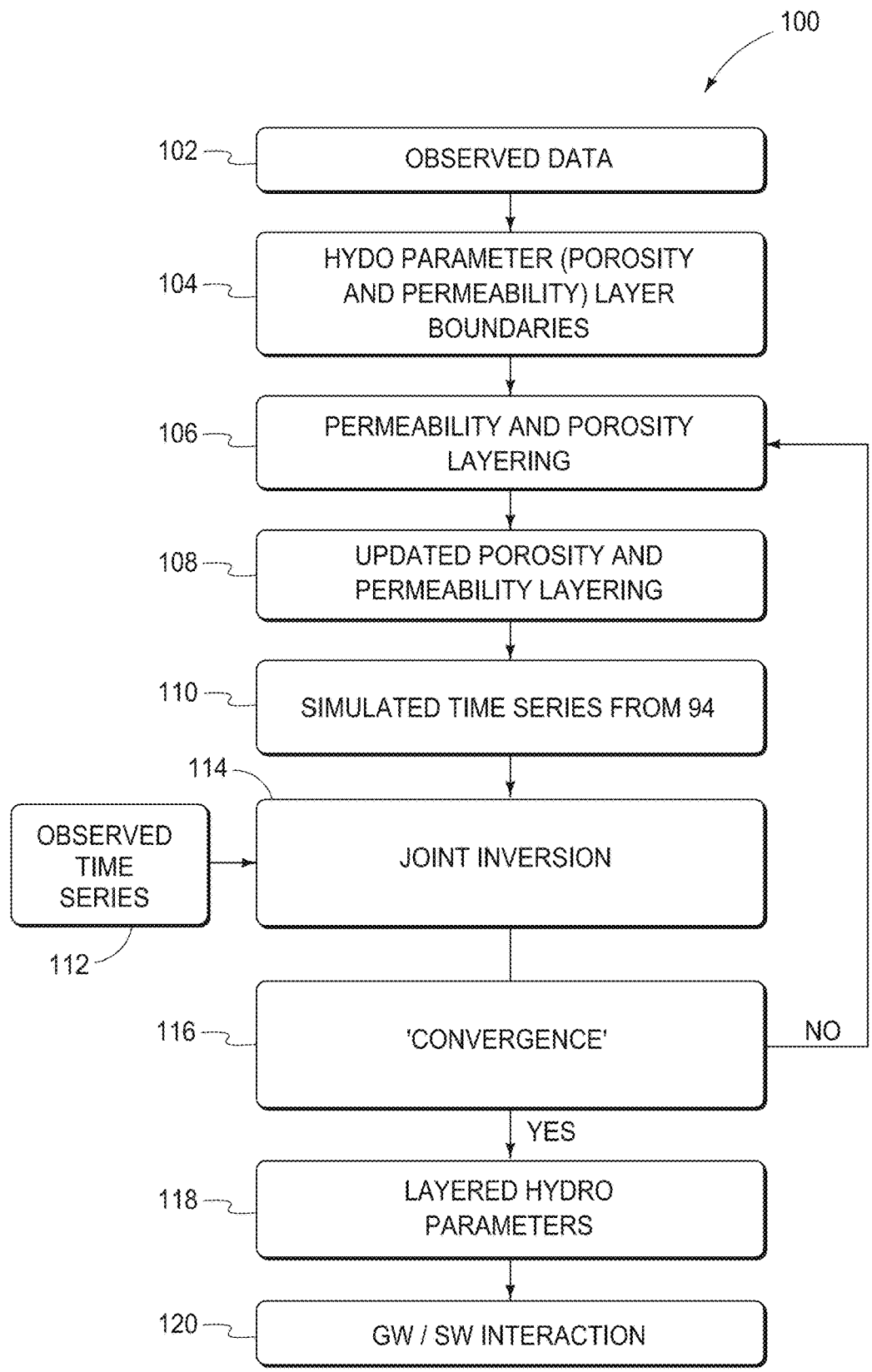
FIG. 9 is another portion of methods for determining SW/GW interactions according to an embodiment of the disclosure.

Referring next to FIG. 9, and iterative process 100 for fitting observed data with simulated data is provided. At 102 observed data is received from the sensing assembly. At 104, the hydro parameter (porosity and permeability) layer boundaries provided in step 74 of process 71 are provided. At 106, permeability and porosity layering is determined from the processed data. At 108, the permeability and porosity layering of 106 is updated. At 110, the simulated time series data provided in step 94 is received.

At 112, the observed time series data and the simulated time series data are jointly inverted at 114. Joint inversion can include application of a Jacobian Matrix.

The joint inversion estimates layered hydrogeologic model parameters by minimizing $$\Phi = \|W_d(A(m) - d_{obs})\|^2 + \lambda \|W_m(m - m_{apr})\|^2 \tag{23}$$

with data weighting matrix $W_d$, observed data vector $d_{obs}$, regularization parameter $\lambda$, model weighting matrix $W_m$, and apriori model vector $m_{apr}$. Two different approaches can be implementated, the conjugate gradient (CG) method, which belongs to the group of deterministic inversion algorithms, and the ensemble Kalman filter (EnKF), which belongs to the group of stochastic inversion algorithms, to solve the optimization problem Eq. (23).

The nonlinear conjugate gradient algorithm as below in Table 1.

TABLE 1

Nonlinear conjugate gradient algorithm.

Given initial guess $m_0$, predicted data vector $A(m_0)$, Jacobian matrix $F_m$, and tolerance tol_r and tol_b, set at first $r_0 = A(m_0) - d_{obs}$, $\delta_r = \|W_d r_0\|^2$, $r_\delta = \|W_d d_{obs}\|^2$, and $k = 0$. Then:

1    while $\delta_r > \text{tol\_r}^2 r_\delta$
2      $b = F_m^T W_d^T W_d d_{obs} + \lambda W_m^T W_m m_{apr}$
3      $s_k = F_m^T W_d^T W_d r_k + \lambda W_m^T W_m (m_k - m_{apr})$
4      $\delta_k = \|s_k\|^2$, $b_\delta = \|b\|^2$, $p_k = s_k$
5      while $\delta_k > \text{tol\_b}^2 b_\delta$
6        $q_k = F_m p_k$
7        $\alpha_k = \dfrac{\delta_k}{\|W_d q_k\|^2 + \lambda \|W_m p_k\|^2}$

TABLE 1-continued

Nonlinear conjugate gradient algorithm.

| | |
|---|---|
| 8 | $m_{k+1} = m_k - \alpha_k p_k$ |
| 9 | $r_{k+1} = r_k - \alpha_k q_k$ |
| 10 | $s_{k+1} = F_m^T W_d^T W_d r_{k+1} + \lambda W_m^T W_m(m_{k+1} - m_{apr})$ |
| 11 | $\delta_{k+1} = \|s_{k+1}\|^2$, $p_{k+1} = s_{k+1} + \dfrac{\delta_{k+1}}{\delta_k} p_k$ |
| 12 | $k = k + 1$ |
| 13 | end |
| 14 | Compute $A(m_k)$ and $F_m$ |
| 15 | $r_k = A(m_k) - d_{obs}$, $\delta_r = \|W_d r_k\|^2$ |
| 16 | end | with Jacobian matrix $F_m$, data residual $r_k$, steepest ascent direction $s_k$, conjugate gradient $p_k$, and iteration number k. For 1D inversions $F_m$ can be computed using a finite difference approximation. There are two loops in the CG algorithm. The main outer loop updates predicted data and Jacobian matrix; the inner loop solves a localized linear system iteratively.

The nonlinear ensemble Kalman filter algorithm is described below with introduction of the following matrix notations $M_0 = [m_0 + u^{(1)}, \ldots, m_0 + u^{(N_s)}] = [m_0^{(i)}]$, $D_{obs} = [d_{obs} + v^{(1)}, \ldots, d_{obs} + v^{(N_s)}] = [d_{obs}^{(i)}]$, $M_{apr} = [m_{apr} + w^{(1)}, \ldots, m_{apr} + w^{(N_s)}] = [m_{apr}^{(i)}]$, where $M_0$ is the initial ensemble matrix of the size $N_c \times N_s$ with mean $m_0$ and covariance Q, $D_{obs}$ is the observed data matrix of the size $N_d \times N_s$ with mean $d_{obs}$ and covariance $R = (W_d^T W_d)^{-1}$, $M_{apr}$ is the apriori model matrix of the size $N_c \times N_s$ with mean $m_{apr}$ and covariance $S = (\lambda W_m^T W_m)^{-1}$, and $u^{(i)}$, $v^{(i)}$, and $w^{(i)}$ are Gaussian distributed random vectors in the ith column, i=1, ..., $N_s$. Vectors $m_0^{(i)}$, $d_{obs}^{(i)}$, and $m_{apr}^{(i)}$ are therefore $m_0$, $d_{obs}$, and $m_{apr}$ plus random vectors of $u^{(i)}$, $v^{(i)}$, and $w^{(i)}$, respectively.

TABLE 2

Nonlinear ensemble Kalman filter algorithm

Given initial guess $M_0 = [m_0^{(i)}]$, predicted data vector $A(m_0)$, matrix $D_0 = [d_0^{(i)}] = [A(m_0^{(i)})]$, and tolerance tol_r, set at first $\delta_r = \|W_d(A(m_0) - d_{obs})\|^2$, $r_\delta = \|W_d d_{obs}\|$, k = 0. then:

| | |
|---|---|
| 1 | while $\delta_r >$ tol_r$^2 r_\delta$ |
| 2 | $\Delta M_k = \left[ m_k^{(i)} - \dfrac{1}{N_s}(M_k e_{N_s \times 1}) e_{1 \times N_s} \right]$ |
| 3 | $\Delta D_k = \left[ d_k^{(i)} - \dfrac{1}{N_s}(D_k e_{N_s \times 1}) e_{1 \times N_s} \right]$ |
| 4 | $P_k = \dfrac{\Delta D_k \Delta D_k^T}{N_s - 1} + R$ |
| 5 | $M_{k+\frac{1}{2}} = M_k - \dfrac{\Delta M_k \Delta D_k^T}{N_s - 1} P_k^{-1}(D_k - D_{obs})$ |
| 6 | $\Delta M_{k+\frac{1}{2}} = \left[ m_{k+\frac{1}{2}}^{(i)} - \dfrac{1}{N_s} \sum_{i=1}^{N_s} m_{k+\frac{1}{2}}^{(i)} \right]$ |
| 7 | $P_{k+\frac{1}{2}} = \dfrac{\Delta M_{k+\frac{1}{2}} \Delta M_{k+\frac{1}{2}}^T}{N_s - 1} + S$ |
| 8 | $M_{k+1} = M_{k+\frac{1}{2}} - \dfrac{\Delta M_{k+\frac{1}{2}} \Delta M_{k+\frac{1}{2}}^T}{N_s - 1} P_{k+\frac{1}{2}}^{-1}\left( M_{k+\frac{1}{2}} - M_{apr} \right)$ |
| 9 | $m_{k+1} = \dfrac{1}{N_s}(M_{k+1} e_{N_s \times 1})$ |
| 10 | $k = k + 1$ |
| 11 | Compute $A(m_k)$ and $D_k = [d_k^{(i)}] = [A(m_k^{(i)})]$ |
| 12 | $r_k = A(m_k) - d_{obs}$, $\delta_r = \|W_d r_k\|^2$ |
| 13 | end | where e denotes the matrix of all ones of indicated size. The EnKF algorithm has only one loop (i.e. the main outer loop) that updates predicted data vector and matrix. The inner loop collapses because direct method of matrix inversion is evolved, for example, $$M_{k+\frac{1}{2}} = M_k - \frac{\Delta M_k \Delta D_k^T}{N_s - 1}\left( \frac{\Delta D_k \Delta D_k^T}{N_s - 1} + R \right)^{-1}(D_k - D_{obs}). \quad (24)$$

The regularization can be treated as a second data set to be fit in the EnKF algorithm (lines 6 to 8 in Table 2). This so-called two-stage EnKF is based on the principle that assimilating two independent observations jointly gives the same result as assimilating them sequentially. Alternatively, one can arrange the measurements and regularization into an augmented data, and then perform assimilation on this new data in a similar way. In such a case, an equivalent formulation of (24) is worth considering for problems with increased data size $$M_{k+\frac{1}{2}} = M_k - \Delta M_k \left(\Delta D_k^T R^{-1} \Delta D_k + (N_s - 1) I_{N_s}\right)^{-1} \Delta D_k^T R^{-1}(D_k - D_{obs}), \quad (25)$$

where I denotes the identity matrix of indicated size. To achieve an efficient inversion, Equation (24) is suggested when $N_d \ll N_s$, and Eq. (25) is recommended when $N_s \ll N_d$. Cholesky decomposition can be further used for a more economical matrix inversion. For completeness, the CG and EnKF algorithms with regularization are provided above. In the case of overdetermined systems (e.g. 1D inversion of the flux tool data), regularization can be skipped by setting $\alpha=0$. The EnKF provides uncertainty of parameter estimates, which is drawn from the ensemble variance after data assimilation. However, the uncertainty becomes trivial in overdetermined problems, especially for inverting the flux tool data since redundant measurements are heavily introduced by time-lapse monitoring.

Let $C_m = \Delta M_k \Delta M_k^T/(N_s - 1)$ denote the model covariance prior to data assimilation at iteration number k. By representing $\Delta D_k \approx F_m \Delta M_k$, we can rewrite Eq. (24) as the following data space Gauss-Newton formula $$M_{k+\frac{1}{2}} = M_k - C_m F_m^T \left( F_m C_m F_m^T + R \right)^{-1}(D_k - D_{obs}). \quad (26)$$

Similarly Equation (25) can be rearranged into the model space Gauss-Newton formula $$M_{k+\frac{1}{2}} = M_k - (F_m^T R^{-1} F_m + C_m^{-1})^{-1} F_m^T R^{-1}(D_k - D_{obs}), \qquad (27)$$

where $F_m$ is the Jacobian of operator A with respect to $m_k$. Equations (26) and (27) indicate that the EnKF algorithm is a stochastic implementation of the Gauss-Newton (GN) method. As a result, the EnKF inherits both advantages and disadvantages of the GN method with respect to convergence, e.g., superlinear convergence rate near the solution, local minima due to improper initial guess, step length adjustment for nonlinear inversions, etc. There are two major differences in the implementation of the GN and the EnKF algorithms. First, the prior model covariance $C_m$ does not change in the GN iteration but is continuously updated in the EnKF. Second, the EnKF does not require an explicit form of the Jacobian matrix. For example, it approximates $F_m C_m F_m^T$ by $\Delta D_k \Delta D_k^T/(N_s-1)$ without evaluating $F_m$.

Referring again to FIG. 9, at 116 convergence of the simulated and observed data is determined using the processing circuitry. Accordingly, converging the data determines if the observed and simulated data match to an accuracy consistent with the noise observed in the time series data. If yes, the process continues to 118 where layered hydro parameters are provided and then the SW/GW interaction provided at 120. If no, the process returns to 106.

Figure 10:
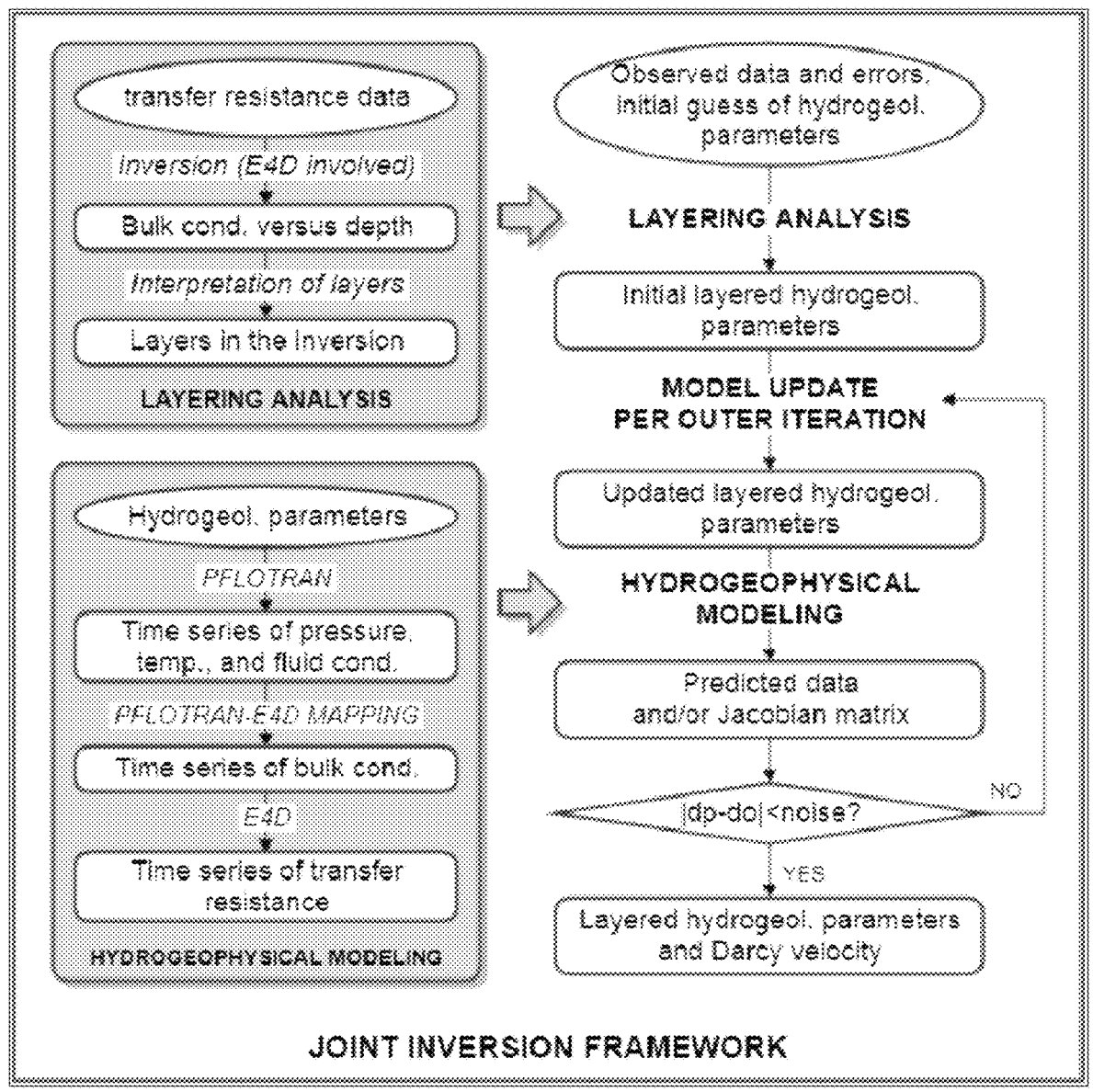
FIG. 10 is a portion of methods for determining SW/GW interactions according to an embodiment of the disclosure.

In accordance with example implementations, a joint inversion framework can be orchestrated within processing circuitry 42. Referring to FIG. 10, a joint inversion framework is shown. The joint inversion framework for the system is summarized in FIG. 10, which depicts of three main parts, layering analysis, model update per outer iteration, and hydrogeophysical modeling. In the layering analysis, transfer resistance data are inverted with E4D to derive vertical bulk conductivity distribution. The bulk conductivity profile is then analyzed to choose the number and thickness of layers in the inversion domain. In the model update per outer iteration, either the CG or EnKF algorithm (lines 2 to 13 in Table 1 or lines 2 to 10 in Table 2) is used to update the hydrogeologic model of permeability and porosity. In the hydrogeophysical modeling, PFLOTRAN is first used for forward flow simulations with the transient boundary and initial conditions of pressure, temperature, and fluid conductivity measured by the flux tool. After mapping the simulated fluid conductivity and estimated porosity from PFLOTRAN to E4D mesh, transient bulk conductivity is computed using Archie's law, and E4D is called to simulate the time-lapse transfer resistance data. A time-interpolation approach can be used to accelerate time-lapse transfer resistance simulation. The model update per outer iteration and hydrogeophysical modeling are repeated until the difference between the predicted and observed flux tool data is less than the noise level.

Computational time of the CG and EnKF algorithms greatly depends on the efficiency of the hydrogeophysical modeling, especially the time-lapse ERT simulation. The CG needs $N_m$ runs of hydrogeophysical modeling to compute the Jacobian matrix, while the EnKF requires $N_s$ runs of hydrogeophysical modeling to calculate the predicted data of ensemble, per outer iteration in an inversion. Each hydrogeophysical modeling calls PFLOTRAN once and E4D $N_t$ times. Even with 1D models, the time-lapse ERT simulation is 3D due to the use of ring electrodes and the cavity caused by the flux tool measuring within the sediment. This results in time-consuming modeling using E4D. The hydrogeologic modeling is 1D on the other hand.

A time-interpolation technique to speed up the 3D time-lapse ERT simulation for 1D models is provided. The time-interpolation of fluid resistivity (reciprocal of fluid conductivity) time series at depth z $$\rho_w(z, t_j) = \sum_{k=1}^{N_b} c_{jk} \rho_w(z, t_k), \quad j = 1, \ldots, N_t, \qquad (28)$$

with fluid resistivity $\rho_w$, number of interpolation basis $N_b$, and interpolation coefficient $c_{jk}$ of the kth basis for the jth datum. The set of basis time steps $t_k$, $k=1, \ldots, N_b$, is a subset of the entire time steps $t_j$, $j=1, \ldots, N_t$. Equation (28) holds because the solution (i.e. PFLOTRAN simulated fluid conductivity) of the 1D advection-diffusion equation is the superimposition of a set of error functions under transient boundary conditions. Using the linear relationship between the fluid resistivity and bulk resistivity (reciprocal of bulk conductivity) according to Archie's Law, we can represent bulk resistivity time series at depth z using a similar time-interpolation $$\rho_b(z, t_j) = \sum_{k=1}^{N_b} c_{jk} \rho_b(z, t_k), \quad j = 1, \ldots, N_t, \qquad (29)$$

with bulk resistivity $\rho_b$, and $N_b$, $c_{jk}$, and $t_k$ the same as those in Equation (28).

As the fluid resistivity contrast between the GW and SW is usually small (i.e. less than one order of magnitude), the related bulk resistivity varies in a small range over time. For this small range of temporal variations in bulk resistivity, the transfer resistance time series at depth z is approximately a linear function with respect to the bulk resistivity time series at the same depth. We further reach the following time-interpolation of transfer resistance time series $$R(z, t_j) = \sum_{k=1}^{N_b} c_{jk} R(z, t_k), \quad j = 1, \ldots, N_t, \qquad (30)$$

where $R(z,t_k)=\Delta_e(\sigma_b(z,t_k))$ denote E4D simulated transfer resistance at depth z and basis time steps $t_k$. Once $N_b$, $t_k$, and $c_{jk}$ are known, we can first run E4D to compute $R(z,t_k)$, and then interpolate $R(z,t_k)$ to $R(z,t_j)$ using Eq. (30).

Given the PFLOTRAN-E4D simulated bulk conductivity on E4D mesh over the entire time steps, we use Equation (29) to find $N_b$, $t_k$, and $c_{jk}$. The overall procedure is summarized as follows. (1) Generate an auxiliary 1D mesh z. This is done by discretizing the spatial extent of Wenner-alpha arrays into a uniform grid of $N_z$ cells, with nodes at the electrode positions. The spacing of the auxiliary 1D mesh therefore represents the vertical resolution of the ERT survey. (2) Build bulk resistivity matrix $\rho_b=[ \ldots, \rho_b(z,t_j), \ldots ]$. We interpolate the bulk resistivity from the E4D mesh to the auxiliary 1D mesh at every time step, and arrange the interpolated bulk resistivity into a matrix of the size $N_z \times N_t$, with $N_z \ll N_t$. (3) Find basis time steps $t_k$. QR decomposition with pivoting can be used to find the basis columns of the bulk resistivity matrix. We take $N_b=N_z$ and the basis time steps $t_k$ from the indices of basis columns. (4)

Calculate interpolation coefficients $c_{jk}$. This is done by plugging $N_b$ and $t_k$ into Eq. (23) and solving for $c_{jk}$.

Using the above time-interpolation process, the time-lapse ERT simulation needs $N_b$ times of E4D runs rather than $N_t$, where $N_b=N_z$ is close to the number of spatial transfer resistance measurements. The time-interpolation has enough accuracy when the fluid resistivity contrast between the GW and SW is small (i.e. within one order of magnitude).

In accordance with example implementations, the system can be configured to assess vertical SW/GW transport under conditions of transient flow and heterogeneous sediments (e.g. high-frequency stage fluctuations within the hyporheic zone). The sensing assembly, installed vertically at the SW/GW interface, collects bulk electrical resistance (i.e. transfer resistance) through time at multiple depths. It also records corresponding time series of vertical pressure gradient, streambed temperature, and fluid conductivity. Under vertical flow conditions, analysis of sensing assembly data as described can provide: (1) vertical component of pore velocity, (2) vertical distribution of porosity, (3) vertical Darcy velocity, and (4) vertical distribution of hydraulic conductivity (or the relevant permeability).

Accordingly, a joint inversion method to estimate porosity, permeability, pore velocity and Darcy velocity is provided. The joint inversion can exploit all available data sets towards an integrated hydrogeological model and provide dynamic SW/GW interactions.

Figure 11:
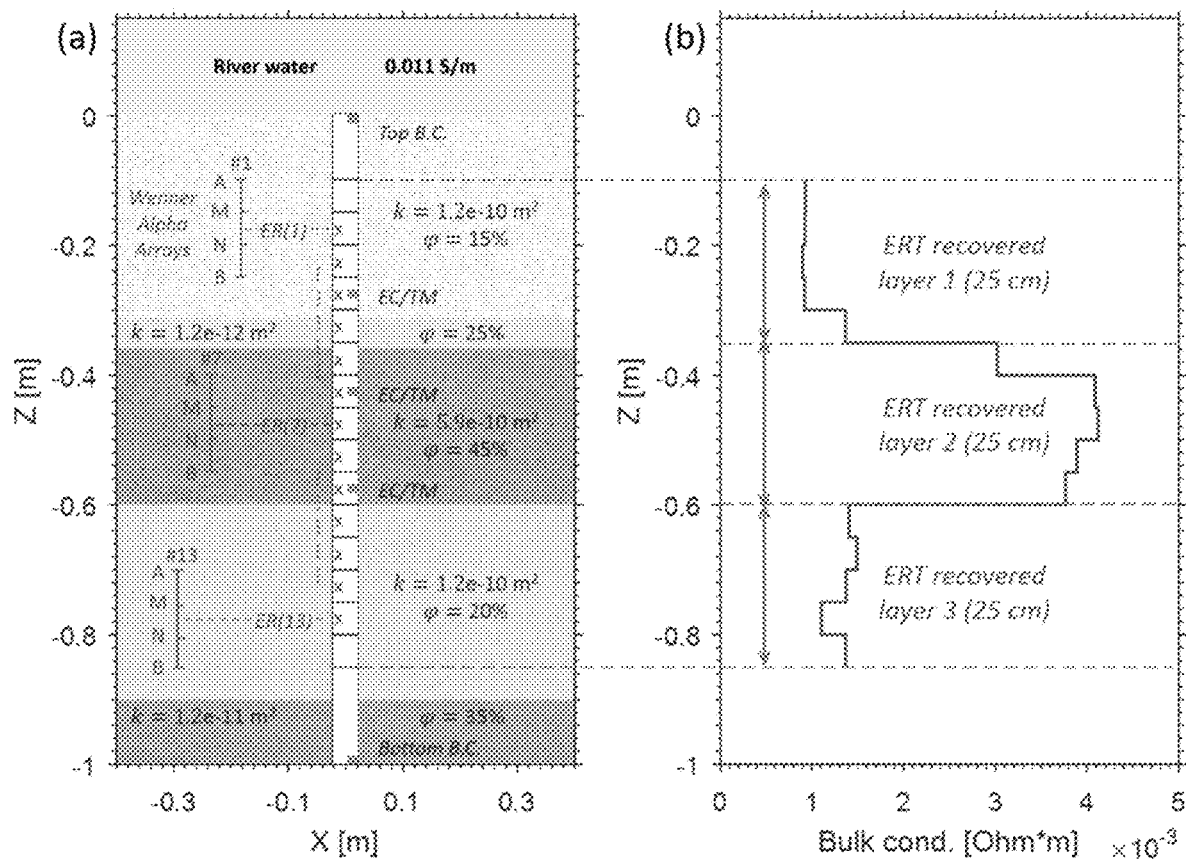
FIG. 11 is modeled data for use in testing the systems of the disclosure.

Referring to FIG. 11, layered hydrogeologic model (a) and vertical ERT inverted bulk conductivity profile (b) is shown. The model depicts of five layers between z=−1 to 0 m, with orange squares the depth of fluid conductivity and temperature sensors, and blue diagonal crosses the center of Wenner-alpha arrays. The vertical bulk conductivity profile was conservatively interpreted as three layers between z=−0.85 and −0.1 m.

Figure 12:
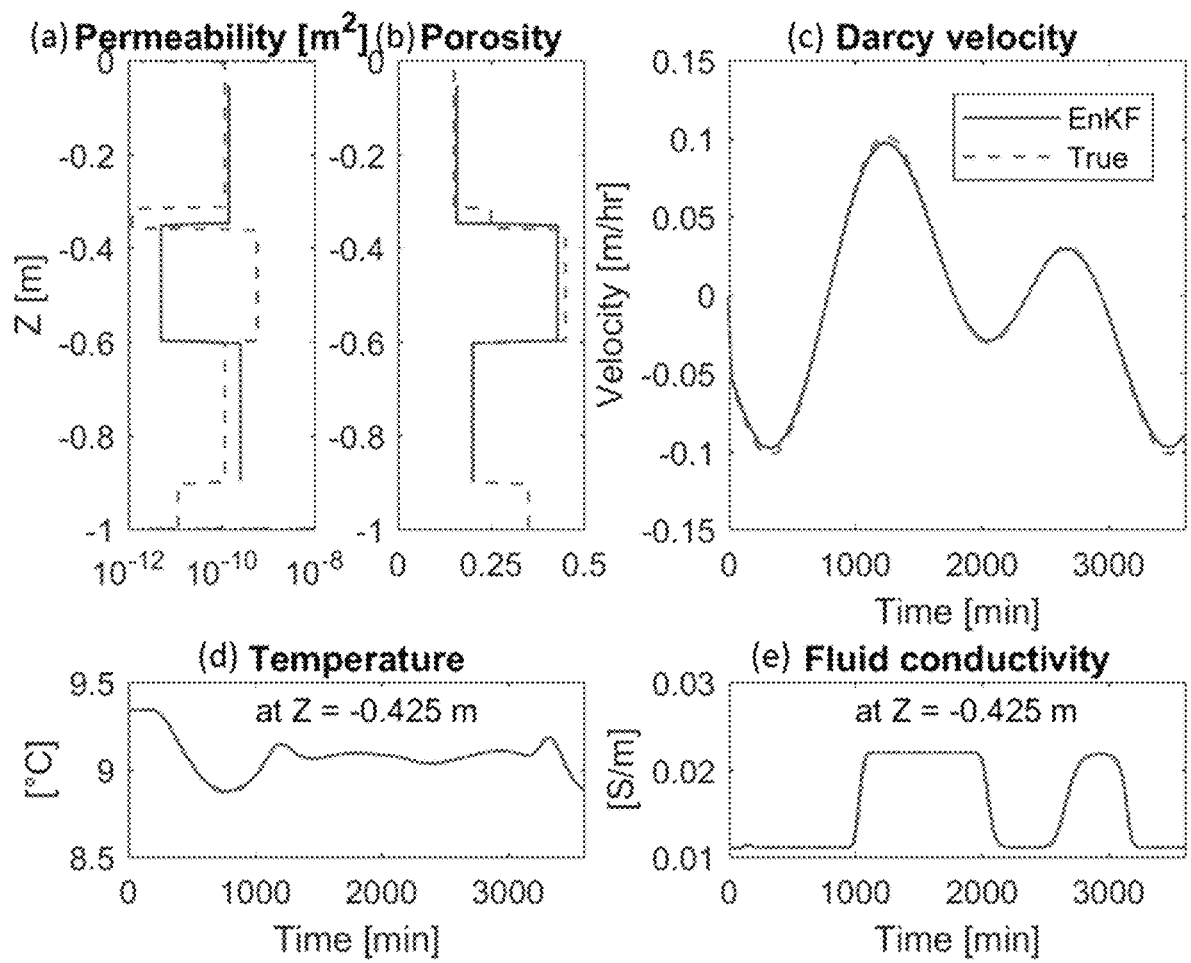
FIG. 12 is modeled data for use in testing the systems of the disclosure.

Referring next to FIG. 12, EnKF results of hydrogeologic modelling (a and b), Darcy velocity (c), temperature (d), and fluid conductivity (f), with ensemble size $N_s$=30 and a relative data misfit of 7.7% are shown. CG result is similar except variations in permeability.

Figure 13:
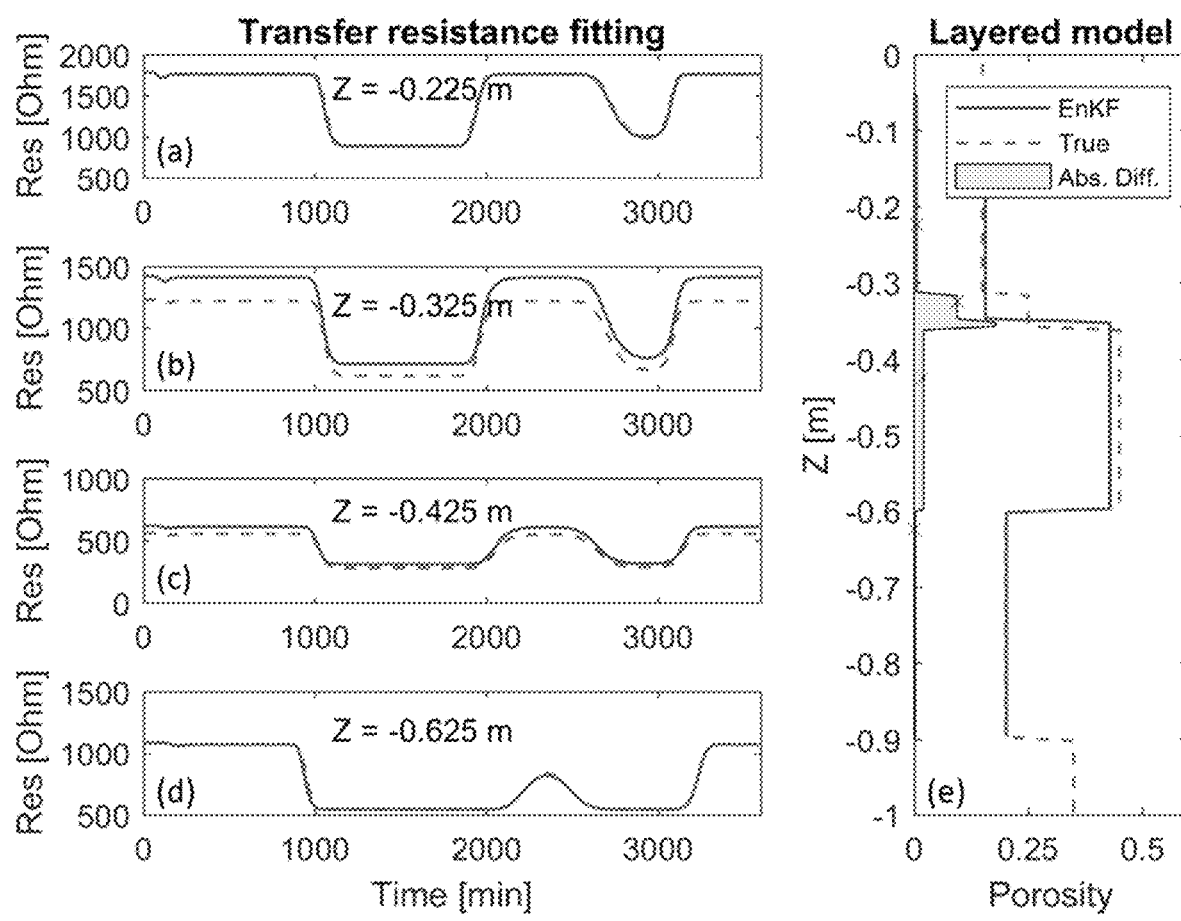
FIG. 13 is fit data using the modeled data according to embodiments of the disclosure.

Referring next to FIG. 13, transfer resistance data fit at different depths using the EnKF algorithm. The largest misfit occurs at the depth between z=−0.36 and −0.32 m, which coincides with that of the estimated porosity. CG result is similar.

TABLE 3

CG and EnKF recovered models.

|  |  | CG algorithm | EnKF algorithm | True model |
|---|---|---|---|---|
| Data misfit |  | 7.66% | 7.72% | — |
| Porosity | top layer | 15.30% | 15.58% | 15% |
|  | mid layer | 43.78% | 42.88% | b/t 25%–45% |
|  | bot layer | 20.43% | 20.19% | 20% |
| Permeability [m²] | top layer | $2.60 \times 10^{-11}$ | $1.45 \times 10^{-10}$ | $1.18 \times 10^{-10}$ |
|  | mid layer | $5.84 \times 10^{-11}$ | $4.95 \times 10^{-12}$ | b/t $1.18 \times 10^{-12}$ $-5.91 \times 10^{-10}$ |
|  | bot layer | $1.13 \times 10^{-11}$ | $2.56 \times 10^{-10}$ | $1.18 \times 10^{-10}$ |
| Average permeability [m²] |  | $1.88 \times 10^{-11}$ | $1.84 \times 10^{-11}$ | $1.92 \times 10^{-11}$ |

Figure 14:
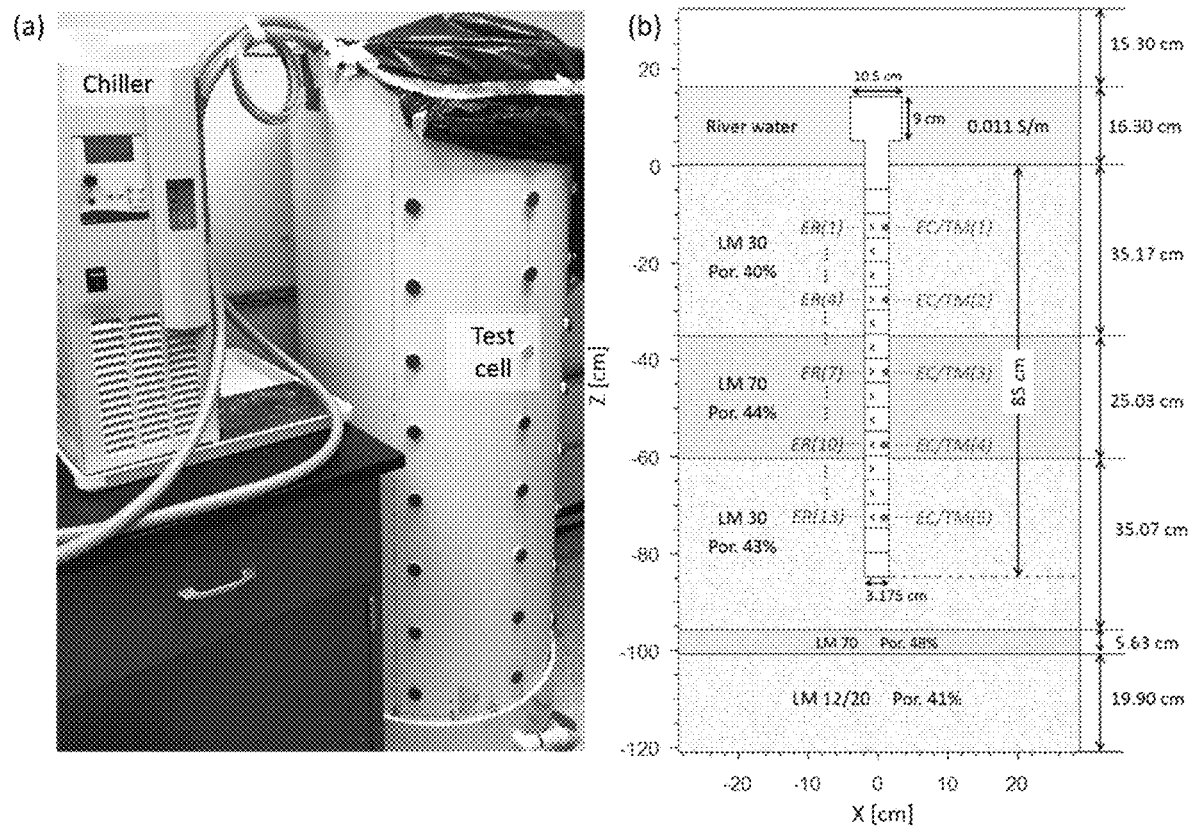
FIG. 14 is an experimental apparatus and sensing assembly configuration according to an embodiment of the disclosure.

SW/GW interactions were simulated in the laboratory using a 1.5 m tall and 0.6 m diameter test cell. The test cell consisted of five sand layers with an accumulated thickness of 1.2 m, as shown in FIG. 14. Exterior (a) and interior (b) of the test cell. The test cell was 1.5 m high and 0.6 m diameter, including five sand layers with a total thickness of 1.2 m. The sensor assembly and system collects time series of vertical pressure gradient, temperature, fluid conductivity and transfer resistance between z=−0.725 and −0.125 m at the positions indicated. (ER: electrical transfer resistance; EC: electrical fluid conductivity; TM: temperature)

Figure 15:
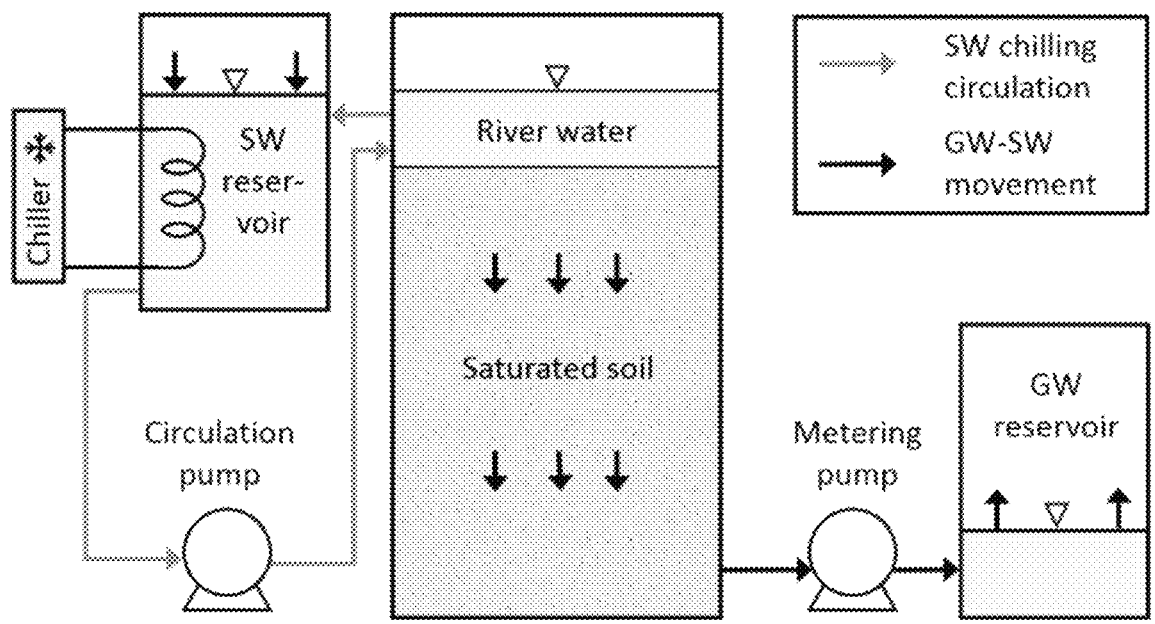
FIG. 15 is another depiction of the experimental apparatus of FIG. 14.

Tap water of different temperature and salinity were used for the surface water and groundwater. The SW reservoir had a temperature of ~10° C. and a conductivity of ~0.011 S/m, while the GW reservoir had a temperature of ~20° C. and a conductivity of ~0.045 S/m. FIG. 15 illustrates the setup of the flow experiment configured for downward flow. During the experiment, surface water is circulating through a chilled reservoir to maintain a temperature of ~10° C. The test cell and the surface water reservoir were coated with foam insulation to minimize the room temperature drift in the measurements.

The sensor assembly was vertically installed across the streambed down to a depth of 0.85 m. Within this depth range, three layers of two types of sand (LM30 and LM70) were encountered. There are 16 ring electrodes between z=−0.8 and −0.05 m, with a vertical spacing of 0.05 m, for the time-lapse ERT survey using Wenner-alpha configuration. Time series of temperature and fluid conductivity are collected at 5 depths between z=−0.725 and −0.125 m, with a vertical spacing of 0.15 m. Besides, the flux tool records pressure difference between z=−0.725 and −0.125 m over time. The top and bottom temperature and fluid conductivity, together with the vertical pressure gradient data, were used to set the transient boundary conditions in the simulation. The rest of data were jointly inverted to estimate the hydrogeologic parameters of the sand column.

The LM30 and LM70 samples (in 5 cm scale) had hydraulic conductivity of 0.148 and 0.0117 cm/s, respectively, which were obtained through constant head tests. With flux, pressure gradient, and length of sample column measured from the constant head tests, hydraulic conductivity was calculated using Darcy's Law. Upscaling of the sample measurements gave an average hydraulic conductivity of 0.0514 cm/s (equivalent to permeability of $5.25 \times 10^{-11}$ m²) for the 0.6 m height sand column next to the flux tool sensors, based on the geometric mean $$K_G = K_{LM30}^{35/60} K_{LM70}^{25/60}.$$

Laboratory measured porosity φ of different layers were given in FIG. 14. These values were calculated by $\varphi=1-\rho_{bulk}/\rho_{particle}$, with the saturated bulk density $\rho_{bulk}$ measured during the packing, and the particle density $\rho_{particle}$ assumed to be 2.65 g/cm³. Porosity of the top three layers (where the sensor assembly was located) were similar and had an average value of 42% for the sediments between z=−0.725 and −0.125 m, based on the arithmetic mean $$\varphi_A = \left(\frac{22.5}{60}\right)\varphi_1 + \left(\frac{25}{60}\right)\varphi_2 + \left(\frac{12.5}{60}\right)\varphi_3,$$

with $\varphi_1$=40%, $\varphi_2$=44%, and $\varphi_3$=43%.

Figure 16:
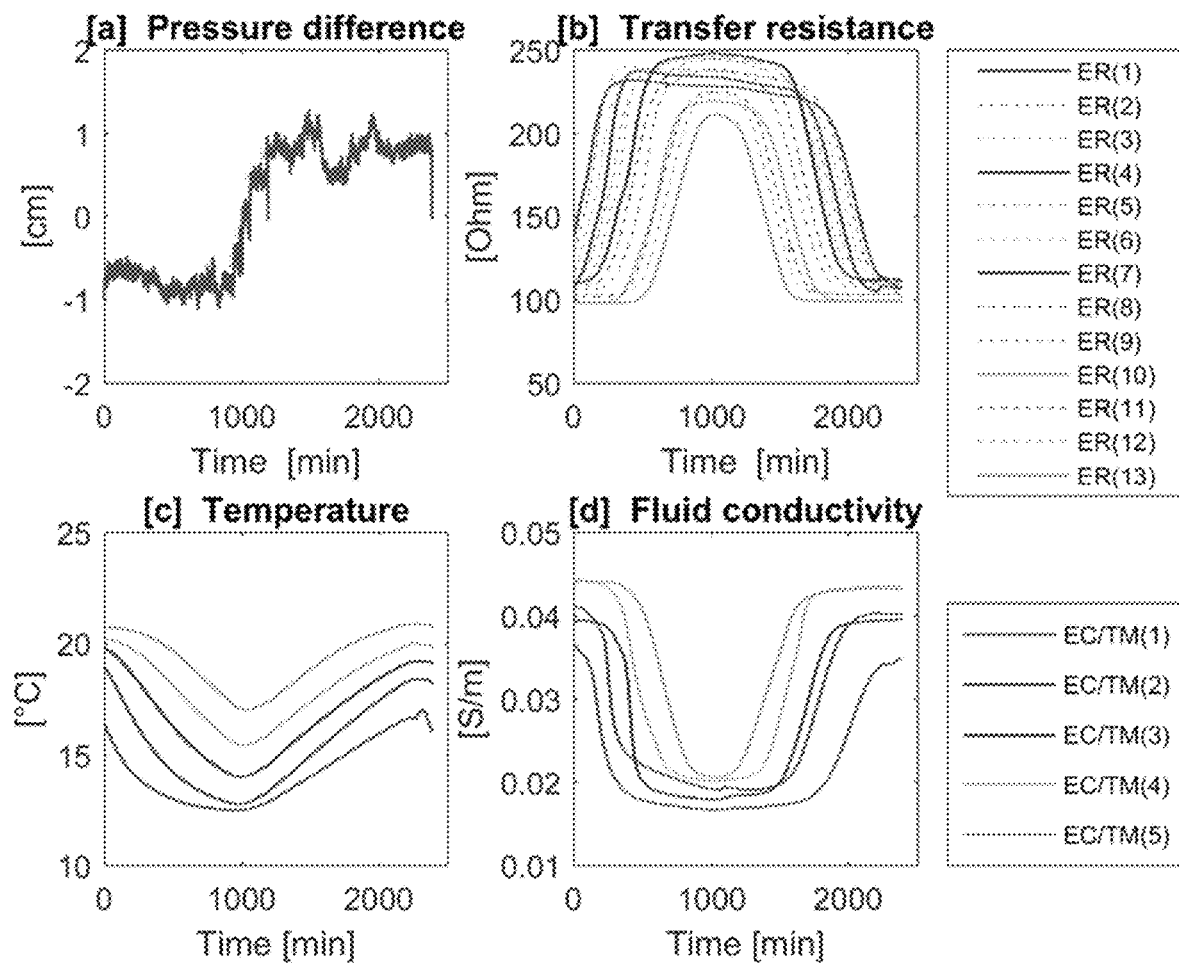
FIG. 16 is data acquired using systems according to embodiments of the disclosure.

Experiment at variable flow rate between −0.06 m/hr and 0.06 m/hr (positive for upward flow), with observed data plotted in FIG. 16. The experiment was (1) started at a downward flow rate of −0.06 m/hr for 16 hours, (2) switched to a slower downward flow rate of ~0.03 m/hr for 1 hours, (3) changed to zero flow rate for 1 hour, (4) restarted at an upward flow rate of ~0.03 m/hr for 2 hours, and (5) switched to a faster upward flow rate of ~0.06 m/hr for 20 hours. A total of forty hours of flux tool data were collected at a time-sampling rate of 1 min.

Figure 17:
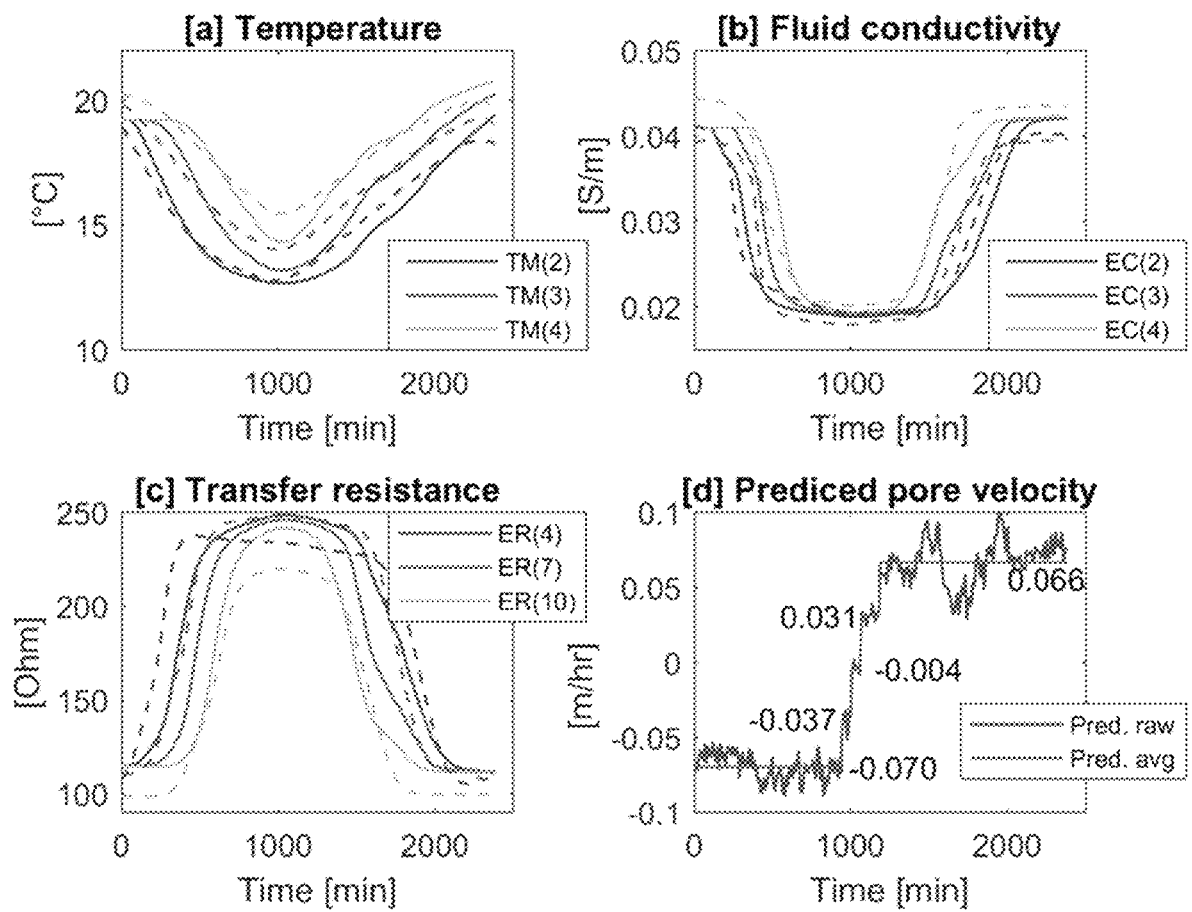
FIG. 17 is data acquired using systems according to embodiments of the disclosure.

The bulk conductivity profile obtained from the ERT inversion suggested one layer between z=−0.725 and −0.125 m, which agreed with the fact that the measured porosity within this depth range did not show obvious layering. Time series of temperature, fluid conductivity, and transfer resistance were then jointly inverted for a homogeneous hydrogeologic model between z=−0.725 to −0.125 m. The joint inversion recovered an average permeability $6.60 \times 10^{-11}$ m$^2$ and porosity 42.08%, with a relative data misfit of 9.4%. The system data fit and predicted pore velocity are shown in FIG. 17. Compared to the measured values, the joint inversion recovered an exact average porosity but higher permeability (25.71% higher), indicating fast flowpaths in the measurements. The fast flowpaths are possibly caused by fluid passing through the fluid conductivity sensor ports. This is a design flaw that will be addressed in the next generation of the tool design.

The sampling volumes of the fluid conductivity and bulk conductivity sensors are different. The pore velocity related to the breakthrough of the fluid conductivity time series represents a local fluid transport, which may be affected by fast flowpaths. In contrast, the breakthrough of the transfer resistance time series characterizes the fluid seepage within a larger volume, which is dominated by flowpaths in the saturated sediments. The forward modeling in the joint inversion does not account for fast flowpaths through the fluid conductivity sensor ports. This may lead to a predicted pore velocity reflecting local fast flowpaths, and thus may result in biased estimation of permeability and Darcy velocity. For example, a better data fit of the fluid conductivity than transfer resistance time series in terms of breakthrough arrival time was found in FIG. 17*b* and FIG. 17*c*. This coincided with larger estimated pore velocity and permeability mentioned above.

Figure 18:
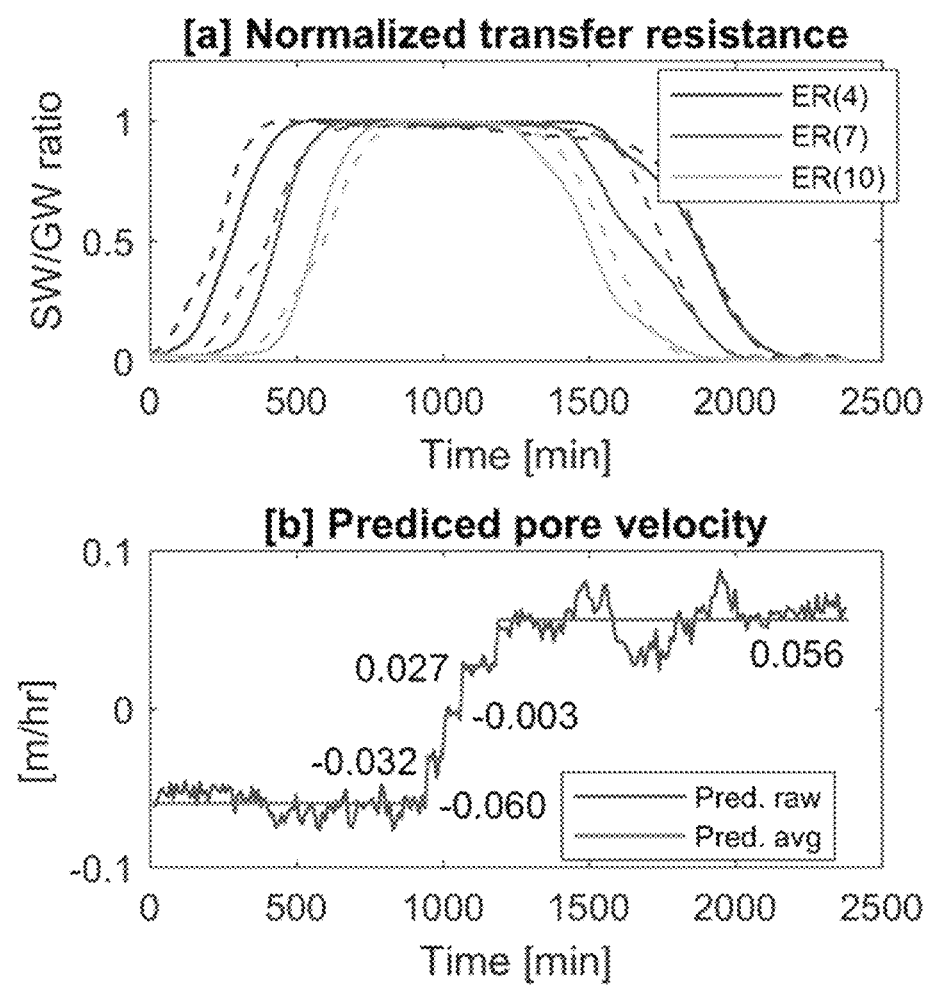
FIG. 18 is data acquired using systems according to embodiments of the disclosure.

An additional inversion for a more accurate estimation of permeability was performed. With porosity fixed as 42%, we converted the measured transfer resistance data to the bulk fluid conductivity and used the "converted bulk conductivity" as the boundary conditions in the PFLOTRAN simulation. Temperature and fluid conductivity were not inverted in this test. The inversion recovered an average permeability of $5.60 \times 10^{-11}$ m$^2$, with a relative data misfit of 8.6%. The predicted transfer resistance and pore velocity can be found in FIG. 18. This time, the estimated permeability and pore velocity are close to the actual values, and the transfer resistance data fit in terms of the breakthrough arrival time were improved. This inversion can be used as a supplementary step of the joint inversion if the fluid conductivity measurements introduce significant local fast flowpaths (i.e., incompatible data fit of fluid conductivity and transfer resistance breakthrough curves).

Figure 19:
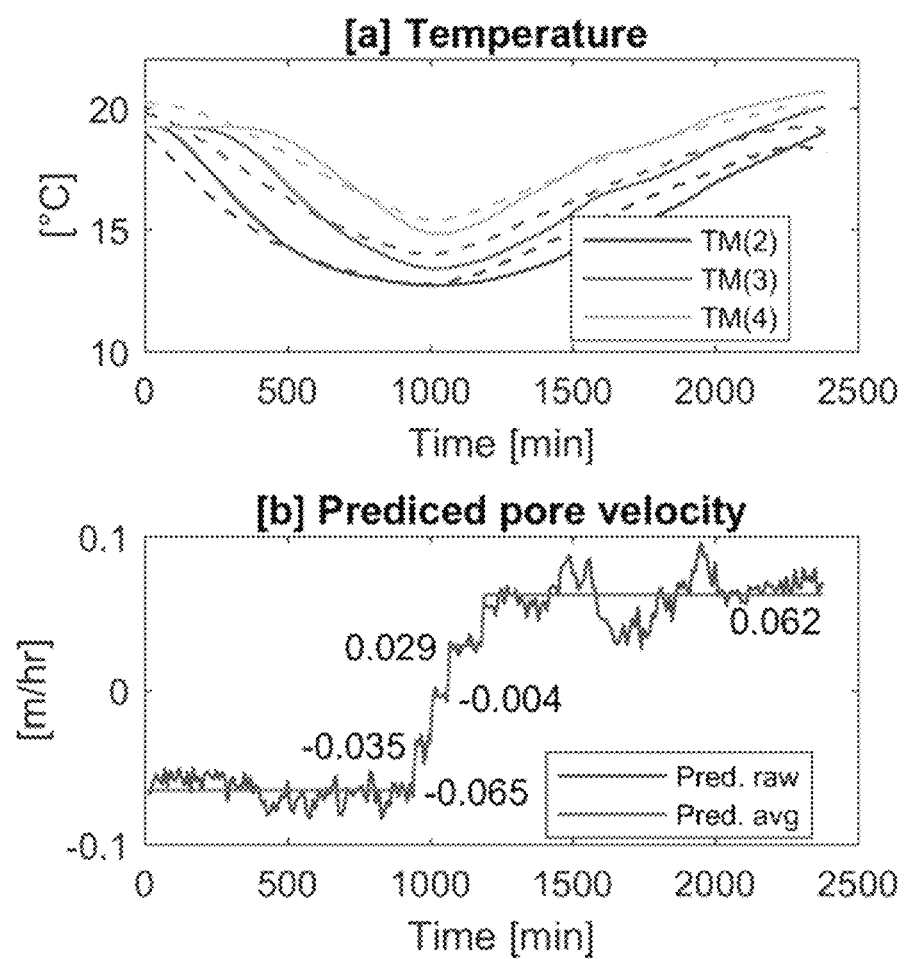
FIG. 19 is data acquired using systems according to embodiments of the disclosure.

It is possible that there is no SW/GW breakthrough in the fluid conductivity and transfer resistance time series, e.g., for constantly upwelling or downwelling streams. For this scenario, the fluid conductivity and transfer resistance data contain only subsurface porosity information. Bulk conductivity obtained from ERT inversion can be correlated with fluid conductivity measurements to calculate porosity through Archie's Law. With porosity estimated and fixed in the hydrogeologic model, the permeability and Darcy velocity can then be derived using the temperature data collected by the embodiments of the systems of the present disclosure. The temperature data can be inverted for permeability, with porosity fixed as 42%. The inversion recovered an average permeability of $6.11 \times 10^{-11}$ m$^2$, with a relative data misfit of 4.1%. The temperature data fit and predicted pore velocity are given in FIG. 19.

Figure 20:
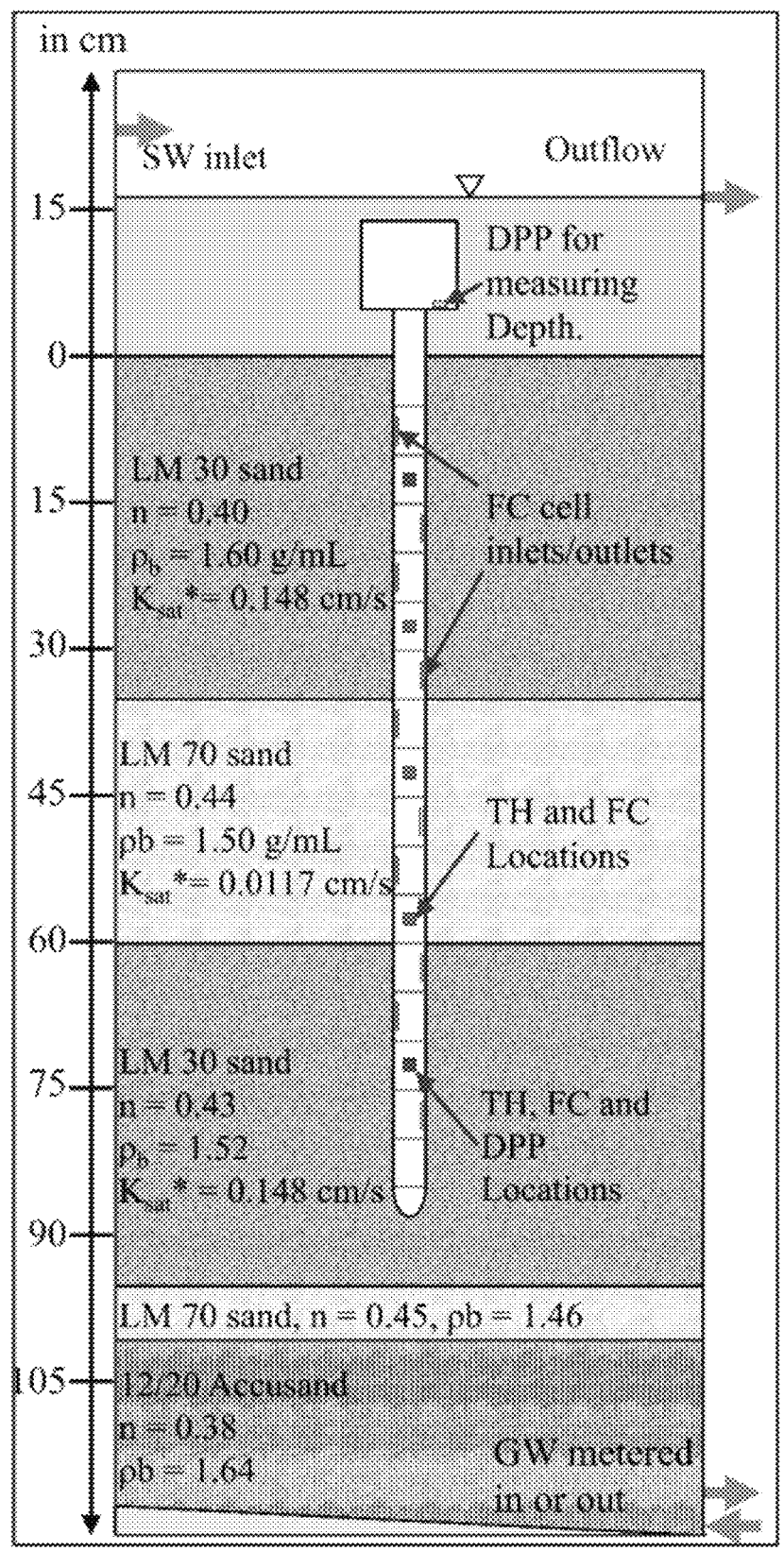
FIG. 20 is another sensing assembly configuration used in combination with an experimental apparatus.

The systems and method of the present disclosure were laboratory tested in a 152 cm tall, 60 cm in diameter insulated soil column. Calculations showed that a large diameter column was necessary to minimize boundary effects on the electrical field produced by the transfer resistance measurement system. In accordance with another experiment, the layering packed around the sensing assembly can be seen in FIG. 20. These layers were packed in 2.5 cm lifts. The bottom two layers of sand labelled 12/20A and LM70 were designed to distribute the flow of water evenly in the column by having a high hydraulically conductive zone, 12/20A, on the bottom and a low conductivity zone, LM70, above it to provide back pressure and distribute flow. The 3rd and 5th layers from the bottom were packed with sand labelled LM30. The fourth layer from the bottom was packed with LM70 sand. A diagram of the probe and layering of each sand type in this test can be seen in FIG. 20.

Three Environmental Tracer experiments were performed using three flow rates (50, 100, and 150 mL/min). For all three of these experiments GW was pumped from the bottom of the soil column into the GW reservoir, pulling SW down through the soil column. This was done until a full breakthrough of SW was observed. Once a full breakthrough was observed the flowrate was reversed at the same rate by pumping GW from the GW reservoir back into the bottom of the soil column.

The 100 mL/min Environmental Tracer experiment was repeated after the fluid conductivity sensor inlets and outlets were modified so that they were separated by 4 cm instead of 10 cm. The only difference between this experiment and the previous 100 mL/min flow rate experiment was the flow was incrementally changed from 100 mL/min downward, to 50 mL/min downward, to zero flow, to 50 mL/min upward and then to 100 mL/min upward where it remained until a full breakthrough of the GW was achieved. Each of the 4 steps was about an hour except there were 2 hours between the 50 and the 100 mL/min upward instead of 1 hour.

For these experiments the temperature corrected bulk resistance measurements were calibrated from bulk conductivity data for the same sand as packed at a similar bulk density and porosity as the sand packed in the soil column. The calibrated bulk conductivity and fluid conductivity peaks of these experiments were used to estimate the porosity.

The temperature corrected transfer resistance measurements were converted to normalized breakthrough curves for the location between the middle electrodes of each 4 electrode resistance measurement. The bulk resistance measured was assumed to increase during the time that the SW front moves between these two electrodes for each of the 13 measurement locations. Therefore, the center of the interval was chosen to extract SW travel times. The breakthrough time was defined as the time at which 0.5 times the total breakthrough magnitude was observed. There may be some error in using the transfer resistance due to changes in the current flow path associated with changes in fluid conductivity within the pore water. However, this should be minimized in this experiment by the similar geometry and porosity within the soil column at various depths canceling out these errors for times between breakthrough curves.

The thermal breakthrough curves of the repeated 100 mL/min experiment were also compared to PFLOTRAN simulated breakthrough curves using the theoretical pore water velocities within the soil column during Experiment 4. The observed and predicted values were evaluated using the coefficient of determination and the root mean square error between the observed and the predicted data.

A Steady-State Thermal Experiment was performed where the SW and GW had the same electrical conductivity but the temperature of the SW remained at 10° C. and GW at room temperature (approx. 21° C.). For this experiment, an upward flow was initiated until thermal equilibrium was reached than the flowrate was increased until steady-state temperature values were collected at 100 and 150 mL/min.

The measured pore water velocities of Experiments 1-3 were all faster than the theoretical values calculated for plug flow through a homogenous porous media. Also, fluid conductivity breakthrough curves had significantly faster pore water velocities than the bulk resistance measurements, indicating that there was a fast flow path through these sensors that had less of an effect on the bulk measurements. The thermistors, being co-located with these fluid conductivity sensors, also may have been affected by this fast flow path. Once a fast flow path was realized, the fluid conductivity sensor port locations were moved from 10 cm apart to 4 cm apart for Experiment 4, which had the same flow rate as Experiment 2. Moving these ports closer together reduces the amount of soil that water passing through the sensor can potentially bypass. The resulting data for Experiment 4, showed measured pore water velocities much closer to the theoretical for both the bulk resistance and fluid conductivity derived values, but even though there is a large improvement in the fluid conductivity derived pore water velocity, a fast flow path is still observed through this sensor. However, with the fast flow path greatly reduced in Experiment 4, the transfer resistance derived pore water velocities are not significantly different than the theoretical. Thus, more weight should be given to pore water velocity values derived using bulk resistance measurements than those derived using fluid conductivity measurements unless the fluid conductivity sensors are improved. Improvement have already been made in the next version which minimize excess flow through these sensors while still providing enough flow to quickly measure changes in fluid conductivity.

The pressure transducers in all of the 4 experiments appeared to have considerable noise. This noise is thought to be from the AC power supply and would most likely be greatly reduced during field deployment where the system will run off of battery and a solar panel. This noise in the pressure transducers measurements was observed to increase when other instruments were running on the same circuit. For the purpose of this study, the pressure measurements were assumed to be constant at a given flowrate so the pressure at each flowrate was averaged. Despite the AC noise, the hydraulic conductivity values from the differential pressure transducer were reasonable and repeatable. This AC noise should not be present when installed in the field as long as clean DC power is used.

TABLE 4

Pore water velocity from breakthrough times of the transfer resistance measurements and the fluid conductivity measurements.

| | $V_{P\_avg}$ (m/hr) | q (m/hr) | % Error |
|---|---|---|---|
| Exp. 1 | | | |
| Theoretical | 0.0277 | 0.0117 | — |
| Measured using Transfer Resistance | 0.0328 | 0.0138 | 18.2% |
| Measured using fluid conductivity | 0.0438 | 0.0184 | 47.3% |
| Exp. 2 | | | |
| Theoretical | 0.0555 | 0.0233 | — |
| Measured using Transfer Resistance | 0.0652 | 0.0274 | 17.4% |
| Measured using fluid conductivity | 0.0842 | 0.0353 | 42.1% |
| Exp. 3 | | | |
| Theoretical | 0.0832 | 0.0349 | — |
| Measured using Transfer Resistance | 0.1023 | 0.0430 | 22.9% |
| Measured using fluid conductivity | 0.1192 | 0.0500 | 39.7% |
| Exp. 4 | | | |
| Theoretical | 0.0555 | 0.0233 | — |
| Measured using Transfer Resistance | 0.0566 | 0.0238 | 1.9% |
| Measured using fluid conductivity | 0.0701 | 0.0294 | 25.3% |

Figure 21:
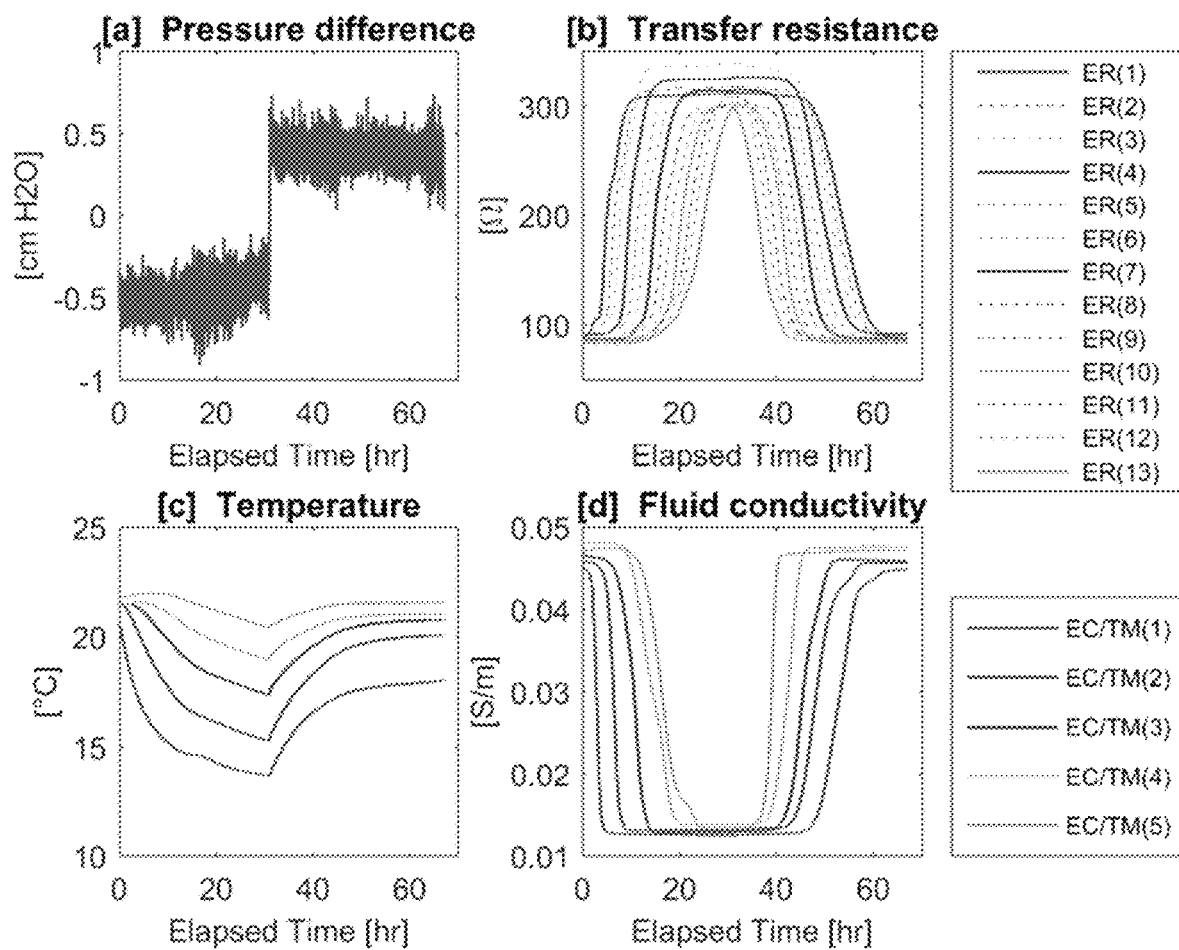
FIG. 21 is data acquired using systems according to embodiments of the disclosure.

Referring to FIG. 21, experimental data collected during Experiment 1 with a flowrate of 50 mL/min is provided where (a.) is the differential pressure between a depth of 12.5 and 72.5 cm below the top of the sediment, (b.) is the transfer resistance measurements of the 13 measurements, (c.) are measurements form temperature sensors TM(1), TM(2), TM(3), TM(4), and TM(5), and (d.) are measurements from fluid conductivity sensors EC(1), EC(2), EC(3), EC(4) and EC(5), which are located at depths of 12.5, 27.5, 42.5, 57.5, and 72.5 cm below the soil surface, respectively.

Figure 22:
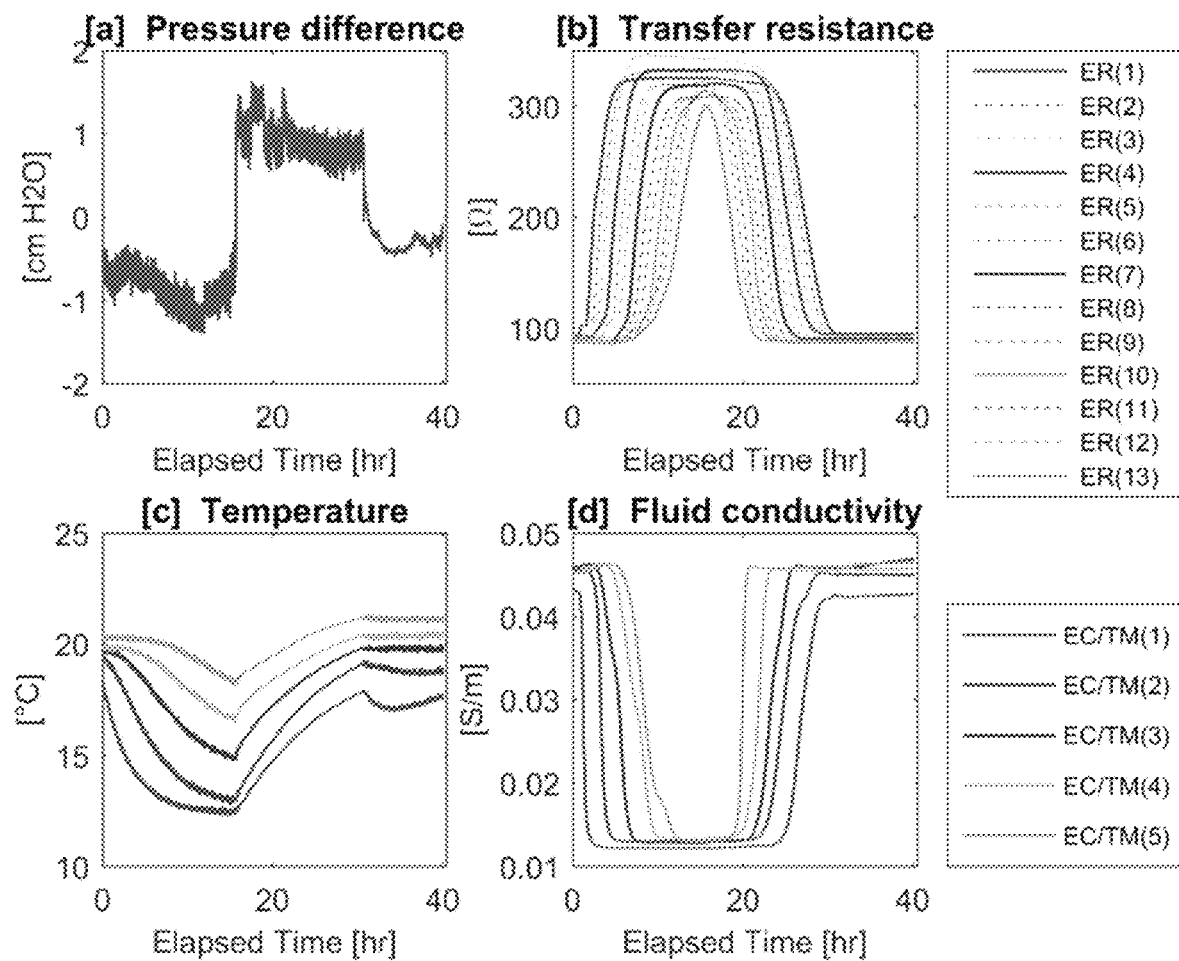
FIG. 22. is data acquired using systems according to embodiments of the disclosure.
Figure 23:
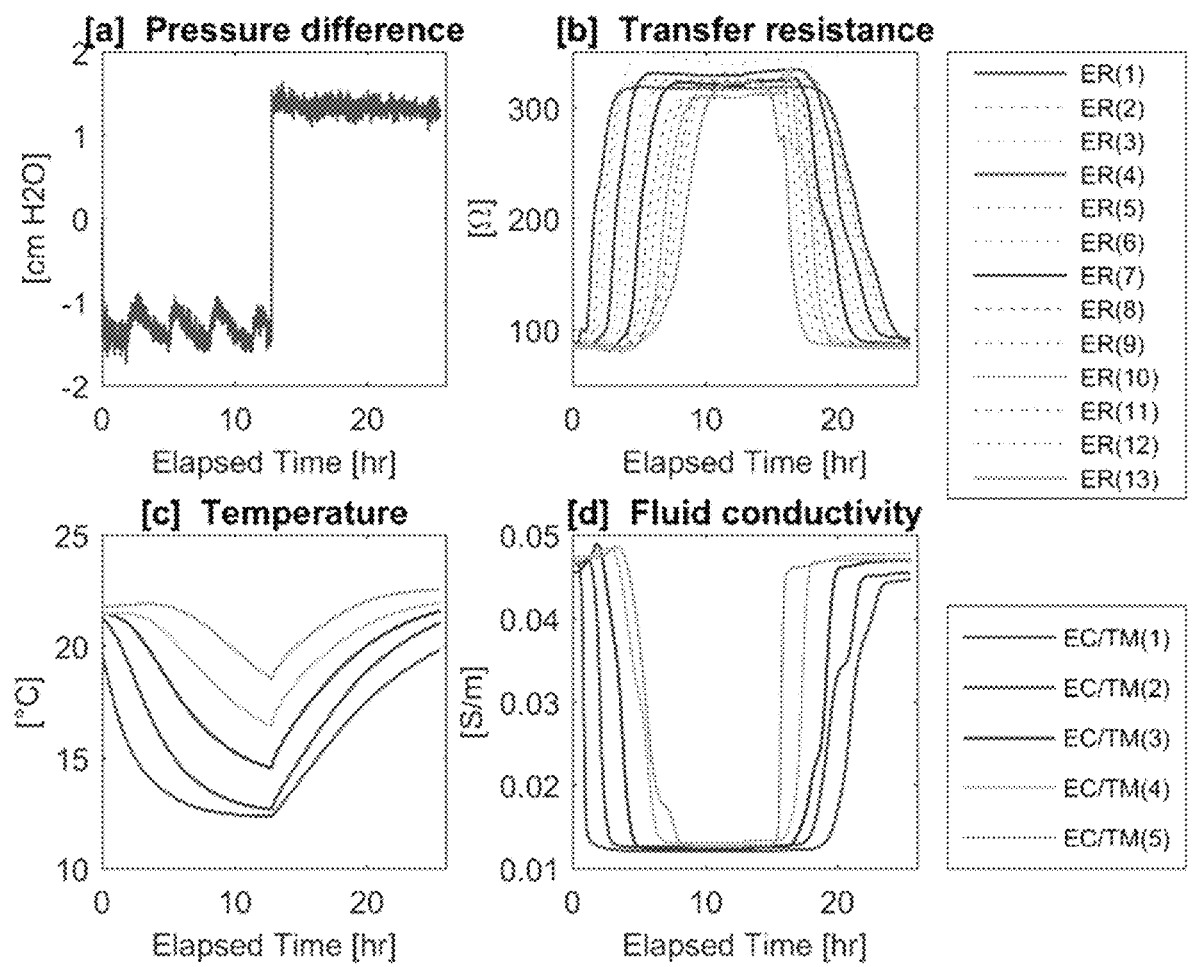
FIG. 23 is data acquired using systems according to embodiments of the disclosure.

Referring to FIG. 22, experimental data collected during Experiment 2 with a flowrate of 100 mL/min is provided where (a.) is the differential pressure between a depth of 12.5 and 72.5 cm below the top of the sediment, (b.) is the bulk resistance measurements of the 13 measurements, (c.) are measurements form temperature sensors TM(1), TM(2), TM(3), TM(4), and TM(5), and (d.) are measurements from fluid conductivity sensors EC(1), EC(2), EC(3), EC(4) and EC(5), which are located at depths of 12.5, 27.5, 42.5, 57.5, and 72.5 cm below the soil surface, respectively.

Referring to FIG. 22, experimental data collected during Experiment 3 with a flowrate of 150 mL/min is provided where (a.) is the differential pressure between a depth of 12.5 and 72.5 cm below the top of the sediment, (b.) is the bulk resistance measurements of the 13 measurements, (c.) are measurements form temperature sensors TM(1), TM(2), TM(3), TM(4), and TM(5), and (d.) are measurements from fluid conductivity sensors EC(1), EC(2), EC(3), EC(4) and EC(5), which are located at depths of 12.5, 27.5, 42.5, 57.5, and 72.5 cm below the soil surface, respectively.

Figure 24:
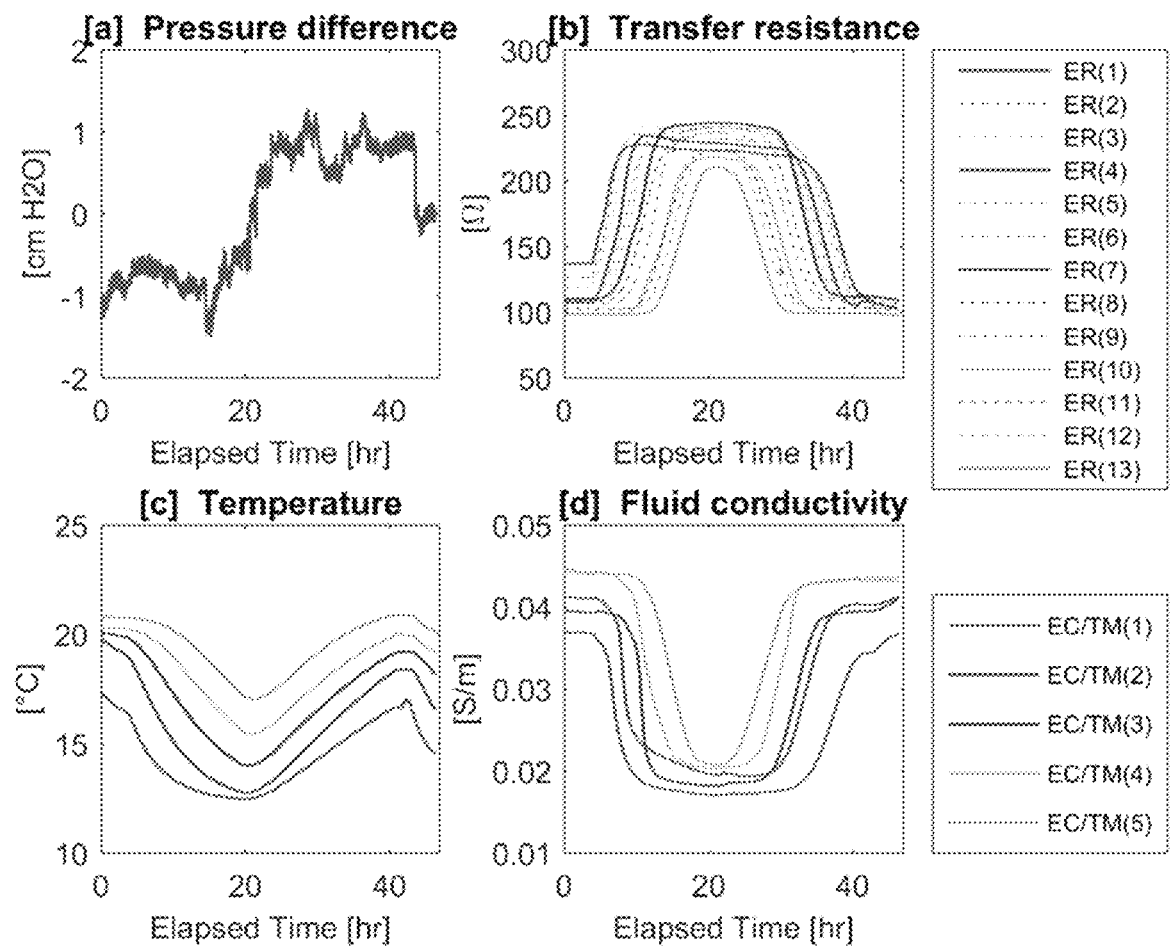
FIG. 24 is data acquired using systems according to embodiments of the disclosure.

Referring to FIG. 24, experimental data collected during Experiment 4 which was a repeat of Experiment 2 after the fluid conductivity sensors were modified and insulation was installed on the outside of the soil column is provided. (a.) is the differential pressure between a depth of 12.5 and 72.5 cm below the top of the sediment, (b.) is the bulk resistance measurements of the 13 measurements, (c.) are measurements form temperature sensors TM(1), TM(2), TM(3), TM(4), and TM(5), and (d.) are measurements from fluid conductivity sensors EC(1), EC(2), EC(3), EC(4) and EC(5), which are located at depths of 12.5, 27.5, 42.5, 57.5, and 72.5 cm below the soil surface, respectively.

In FIGS. 21-24, GW is initially pumped out of the bottom of the test column pulling SW down past the TEFLUX. This is why the pressure starts out negative in FIGS. 21a-23a. Once a full breakthrough of SW was observed, the flow is reversed to pump GW back into the bottom of the column until a full breakthrough of GW is observed. In FIG. 24a the flow is changed in stages to better simulate flow changing directions in a steam bed. In FIGS. 21b-23b the transfer resistance breakthrough curves are closer together than expected because of an observed fast flow path through the fluid conductivity sensors, which was corrected in 24b. This same fast flow path is even more pronounce in FIG. 21d-23d, but was greatly improved in FIG. 24d due to the modifications to the system.

The porosity was estimated using Archie's law parameters where the slope of the fluid electrical conductivity and bulk electrical conductivity were used to calculate the formation factor. The results of these calculations can be seen in Table 5. It is also important to note that the fast flow path in Experiments 1-3 did not negatively affect these porosity measurements because they were only calculated from data where just the SW and GW are observed, and not during breakthroughs of GW or SW. The cementation exponent was assumed to be 1.4 for sand grains close to spherical. The estimated values of porosity based on measured parameters range from −14 to 15 percent of the values calculated from the packing parameters. However, most of the system derived porosity values have absolute errors below 10%, with the exception of the upper most measurement (12.5 cm depth). The upper most measurements may be skewed to a higher porosity because of their proximity to the soil surface. Also between Experiment 3 and 4 the experimental system was removed from the test column for modifications and reinstalled, which may have disturbed some of the packed sediment, thus potentially increasing the error in porosity during experiment 4.

TABLE 5

Porosity estimations using transfer resistance measurements inverted for bulk conductivity and the measured fluid conductivity with an assumed cementation exponent of 1.4. Porosity values calculated from packing parameters were calculated for approximately a 7.5 cm of sand centered on the fluid conductivity locations.

| Depth (cm) | Exp. 1 | % Err | Exp. 2 | % Err | Exp. 3 | % Err | Exp. 4 | % Err | Packing |
|---|---|---|---|---|---|---|---|---|---|
| 12.5 | 0.431 | 8% | 0.453 | 15% | 0.442 | 11% | 0.443 | 12% | 0.394 |
| 27.5 | 0.429 | 3% | 0.399 | −5% | 0.411 | −2% | 0.410 | −2% | 0.411 |
| 42.5 | 0.392 | −9% | 0.406 | −6% | 0.419 | −2% | 0.370 | −14% | 0.421 |
| 57.5 | 0.407 | −12% | 0.424 | −8% | 0.459 | 2% | 0.427 | −7% | 0.451 |
| 72.5 | 0.409 | −4% | 0.416 | −2% | 0.425 | 1% | 0.391 | −8% | 0.416 |
| Average | 0.414 | −3% | 0.420 | −1% | 0.431 | 2% | 0.408 | −4% | 0.419 |

The saturated hydraulic conductivity values calculated for each experiment using the theoretical and the measured differential pressure between the upper and lower pressure ports can be seen in Table 6. These values seem reasonable considering that LM70 and LM30 sand had laboratory measured hydraulic conductivity values of 0.0117 and 0.148 cm s$^{-1}$, respectively. Using the geometric mean for the two above values, the calculated effective vertical hydraulic conductivity was calculated to be 0.0514 cm s$^{-1}$, which appears be close to the measured hydraulic conductivity values seen in Table 6.

TABLE 6

Measured Hydraulic Conductivity for Exp. 1-4

| Experiment | Measured Ksat (cm/s) |
|---|---|
| Exp. 1 | 0.0444 |
| Exp. 2 | 0.0440 |
| Exp. 3 | 0.0442 |
| Exp. 4 | 0.0480 |

Figure 25:
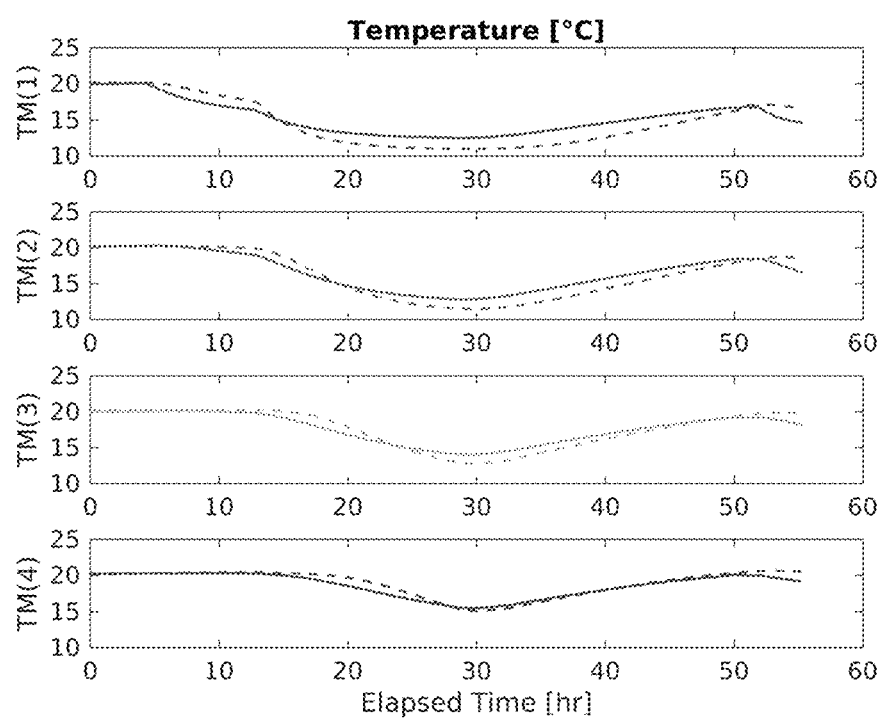
FIG. 25 is data acquired using systems according to embodiments of the disclosure.

PFLOTRAN was used to predict the temperature breakthrough curves for Experiment 4. Parameters used to predict temperature data include porosity and the thermal boundary conditions. The observed and predicted temperatures at 4 thermistor locations [TM(1), TM(2), TM(3), and TM(4)] (seen in FIG. 25) were evaluated using the coefficient of determination and the RMSE between the predicted and observed values. The coefficient of determination was 0.947, 0.966, 0.982, and 0.967 and the RMSE was 0.0908, 0.0244, 0.0015, and 0.0037, respectively. Referring to FIG. 25, observed data from Exp. 4 (solid) and predicted data using PFLOTRAN (dashed). TM(1) is the upper most thermistor and TM(4) is the second thermistor from the bottom are provided. A supplemental thermistor at the top of the sand and the lowest thermistor (TM(5)) were used by PFLOTRAN as boundary conditions for the predicted data. As can be seen in FIG. 25, the observed temperature is generally higher than the predicted for all 4 locations which may be from insufficient insulation around the soil column, but also could have been caused by slight differences between the model parameters and the actual. However, the observed and predicted data appeared to have a good correlation for all 4 thermistor locations indicating that the pore water velocity used in the predicted values must have been close to the actual pore water velocity.

The calculated pore water velocity and Darcy's flux can be seen in Table 7. These values were calculated by fitting a $K_{fs}$ of 3.28 W m−1 K−1 to the data collected and is within the range ranges (2.5-3.4 W m−1 K−1) described by Midttømme and Roaldset (1998) for the saturated sand used these experiments.

TABLE 7

Resulting pore water velocities and Darcy's flux values calculated using the TEFLUX. These values were calculated using the Turcotte and Schubert (1982) model as discuss in Schmidt et al. (2007).

| | Flowrate @ 100 mL/min | | Flowrate @ 150 mL/min | |
|---|---|---|---|---|
| | $V_P$ (m/hr) | q (m/hr) | $V_P$ (m/hr) | q (m/hr) |
| Measured | 0.0564 | 0.0231 | 0.0834 | 0.0333 |
| Theoretical | 0.0555 | 0.0228 | 0.0832 | 0.0333 |

As has been shown, porosity can be calculated using measured Archie's law parameters and can be used to calculate vertical flux from pore water velocity. Most of the porosity values calculated had errors less than 10%, except the upper most porosity values. It is thought that the upper most values may be skewed to a higher porosity because of their proximity to the sand surface boundary. Unless significant laying is observed only one porosity value will be assigned by averaging the measured values. When all 5 values are averaged, the porosity error goes down to less than 5%.

Figure 26:
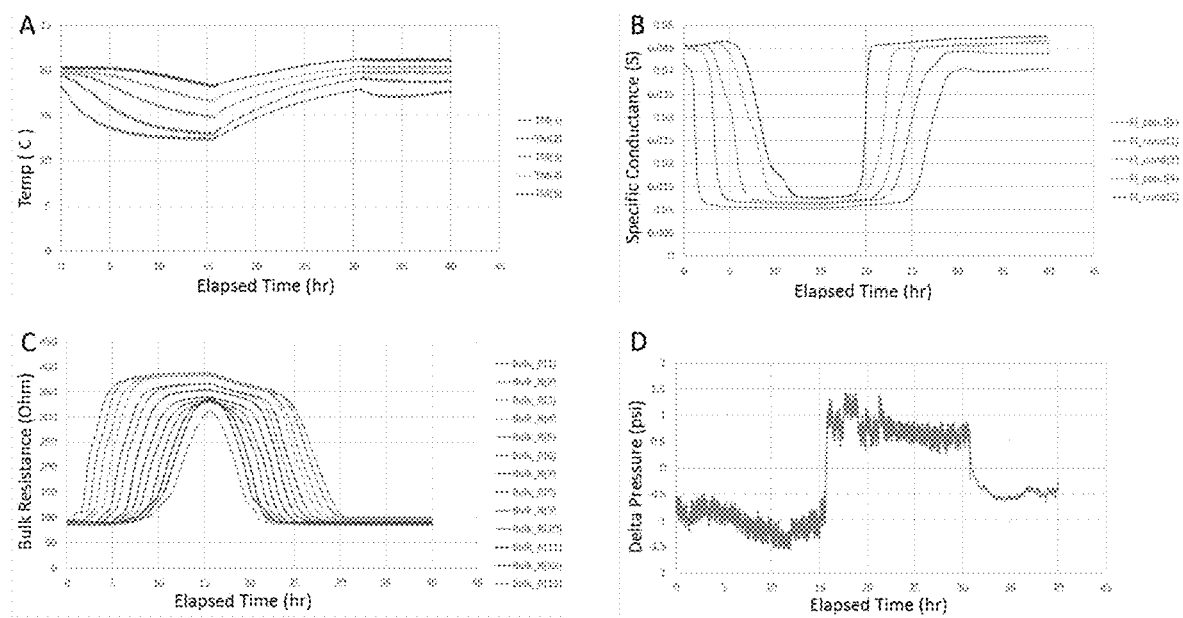
FIG. 26 is data acquired using systems according to embodiments of the disclosure.

FIG. 26 shows example laboratory scale testing data collected the systems and methods of the present disclosure. FIG. 26A shows temperature time-series on each thermistor, FIG. 26B shows the fluid specific conductance time-series, FIG. 26C shows the bulk electrical resistance time-series, and FIG. 26D shows the pressure differential between upper and lower boundary pressure sensor.

Figure 27:
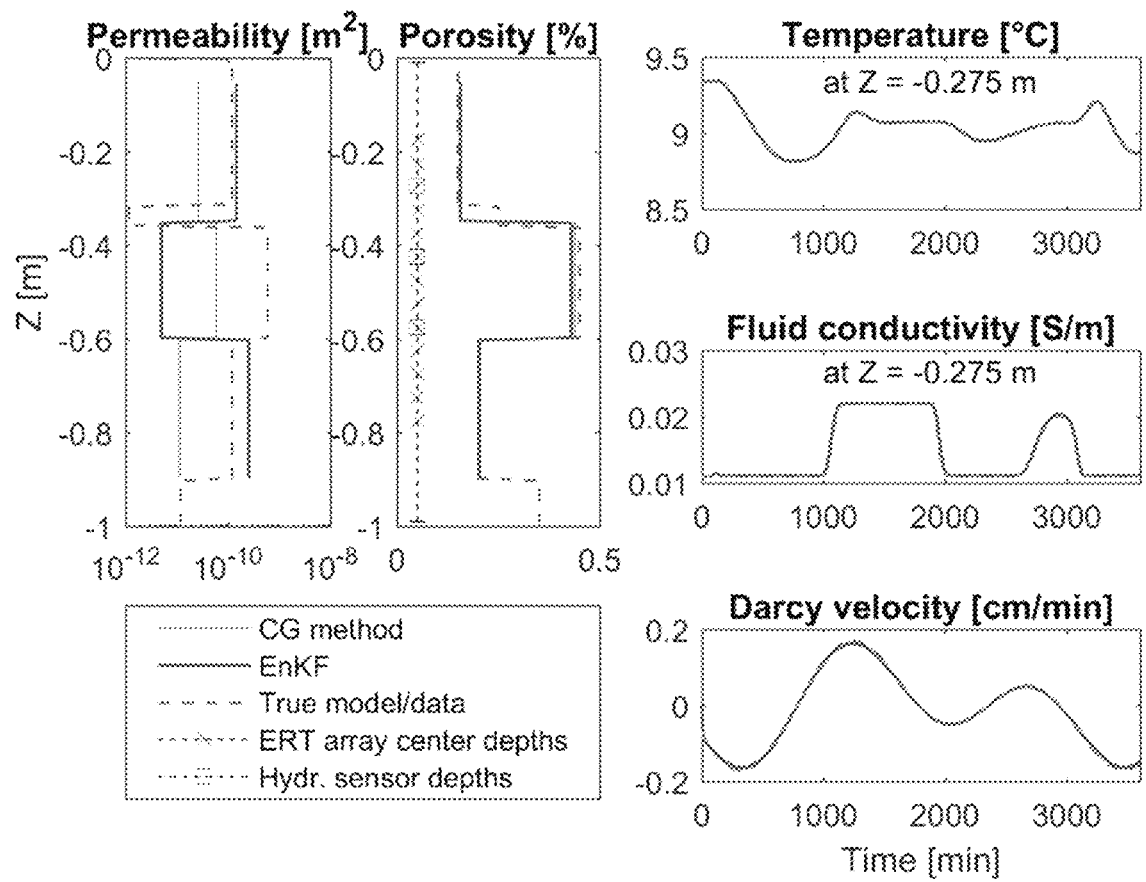
FIG. 27 is data acquired using systems according to embodiments of the disclosure.

To simulate the flux tool survey at the groundwater/surface water interface, we consider a 1D hydrogeological model with vertically varying permeability, k(z), and porosity, φ(z). The 1 m deep synthetic model consists of five layers, with permeability ranging from $1.2 \times 10^{-12}$ to $6 \times 10^{-10}$ $m^2$, and porosity from 0.15 to 0.45, as shown in FIG. 27. A survey configuration using Wenner Alpha array is deployed for the system ERT measurement, whereby the two potential measurement ring electrodes are placed in between the two current ring electrodes, with an equal spacing between any two adjacent ring electrodes. There are a total of 13 Wenner Alpha arrays in the synthetic model measuring time series of transfer resistance, R(z,t), where the array centers are evenly distributed between the depths of 0.175 m and 0.775 m with a vertical spacing of 0.05 m. In addition to the ERT measurement, there are 3 pairs of hydrological sensors measuring time series of temperature, T(z,t), and fluid conductivity, $\sigma_w(z,t)$, at depths of 0.275 m, 0.425 m, and 0.575 m. The entire simulation spans 2.5 days with a time interval of 15 min. Finally, we assume the system records the boundary as well as initial conditions of the pressure, temperature, and fluid conductivity at the top (z=0) and bottom (z=−1 m) of the modeling domain.

Figure 28:
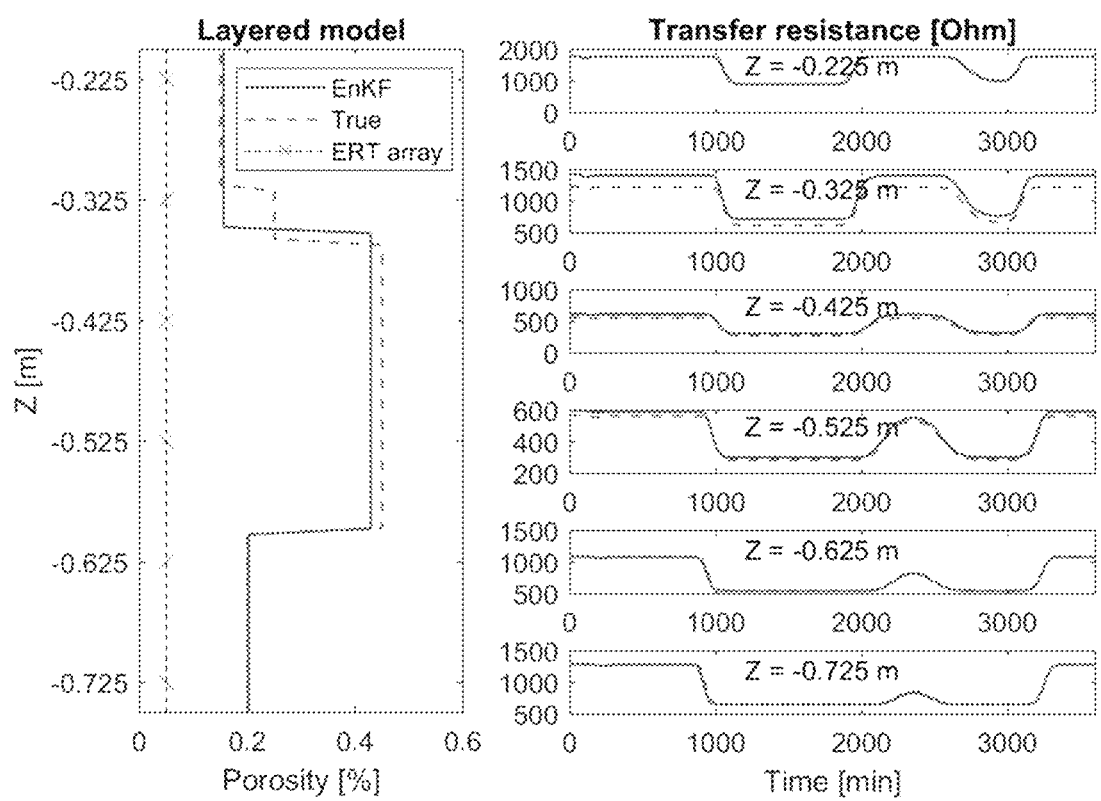
FIG. 28 is data acquired using systems according to embodiments of the disclosure.
Figure 29:
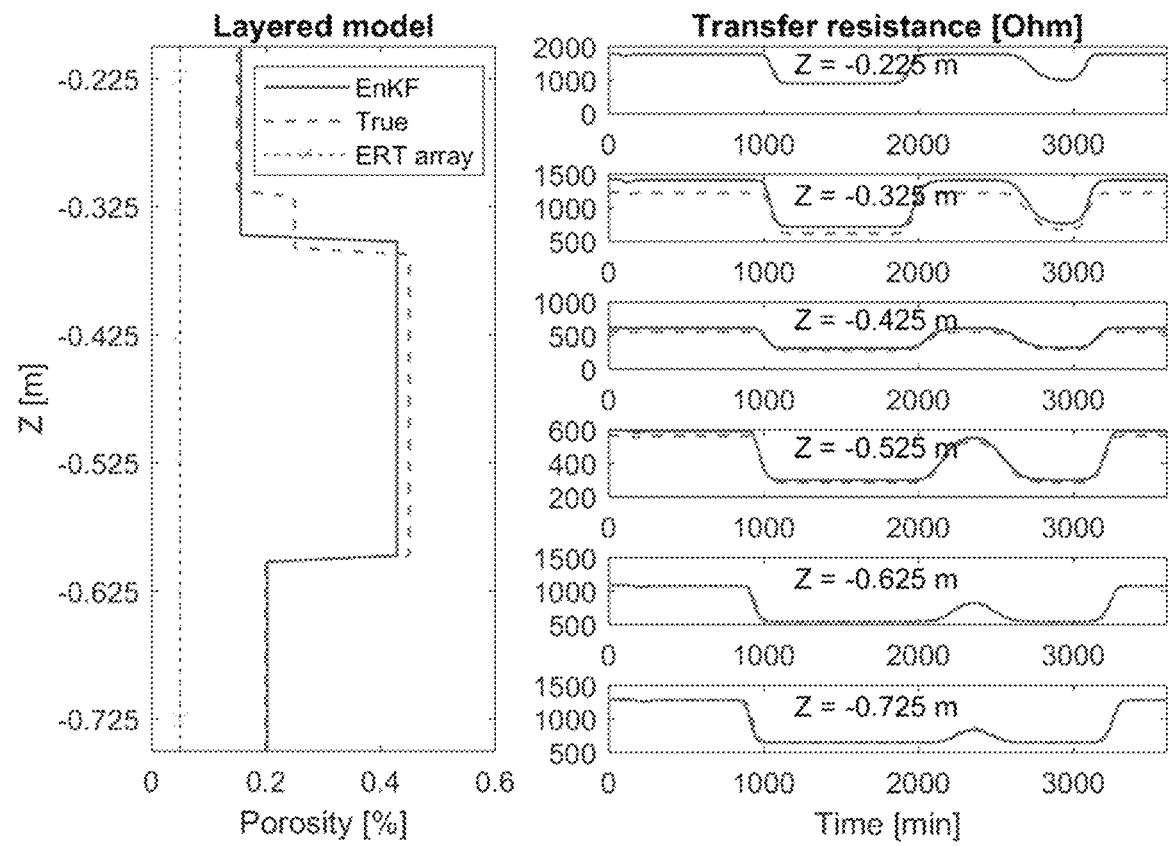

The simulated time series of temperature, fluid conductivity, and transfer resistance, along with the boundary and initial conditions, are used as the input data of the joint inversion. The E4D inversion can be used to obtain the 1D layered mesh, and found three bulk layers between the depths of 0.1 m and 0.8 m, except the thin layer between the depths of 0.3 m and 0.35 m and the bottom layer below the depth of 0.9 m, due to the limit of vertical resolution and survey coverage. The next joint inversion of the hydrological and ERT data estimated permeability and porosity of the three bulk layers. Both the CG and EnKF algorithms produced good data fittings between the predicted and synthetic temperature and fluid conductivity, and accurate estimations of the Darcy velocity, as shown in FIG. 28.

Due to the missing thin layer, the recovered porosity model between the depths of 0.3 m and 0.6 m has certain offset away from the true value. The error in the model space then propagates into the data space, resulting a static shift between the predicted and observed data at corresponding depths throughout the entire simulation time, as shown in FIG. 28. As the center of the Wenner Alpha array moving away from the thin layer and its neighbors, e.g., above the depth of 0.3 m or below the depth of 0.6 m, the static shift goes away and we again obtain good data fitting between the predicted and synthetic transfer resistance.

Unlike the porosity, the missing thin layer in the recovered permeability model does not affect the data fitting. Indeed, the survey design of the sensor rod allows an estimate of the average permeability instead of the permeability variations of the 1D column. Comparison of the CG and EnKF inversions in FIG. 27 indicates that the recovered permeability of the layers is non-unique. However, the average permeability of the two inversion results are similar and close to that of the true model. This can explain why both inversions can fit the overall data at the same level. To confirm the average permeability hypothesis, we ran another test of the joint inversion by using three layers for porosity but one layer for permeability in the 1D mesh. This inversion produced the same data fitting as before, and the recovered permeability of the single bulk layer was close to the average permeability of the true model.

The invention claimed is:

1. A system for determining GW/SW interaction, the system comprising:
   a sensing assembly comprising sensors for pressure, fluid conductivity, temperature, and transfer resistance measurements; and
   processing circuitry operatively coupled to the sensing assembly and configured to receive data from the sensing assembly and process the data to provide a GW/SW interaction, wherein the data includes pressure, fluid conductivity, temperature, transfer resistance data; wherein the sensing assembly includes sets of sensors for each of the measurements.

2. The system of claim 1 wherein the sensing assembly is configured to extend vertically below the GW/SW barrier.

3. The system of claim 1 wherein each sensor in the set is spaced apart from the other sensor in the set a predetermined distance along the sensing assembly.

4. The system of claim 3 wherein the predetermined distance is associated with a depth below the GW/SW barrier.

5. The system of claim 1 wherein the system is configured to provide simulated SW/GW interaction and real time SW/GW interaction, and process those interactions to fit the simulated SW/GW interaction with the real time SW/GW interaction to provide a modified SW/GW interaction.

6. The system of claim 1 wherein the transfer resistance data is processed differently than the pressure, fluid conductivity, and temperature data.

7. The system of claim 6 wherein the transfer resistance data is processed to provide bulk electrical conductivity data.

8. The system of claim 1 wherein the pressure, fluid conductivity, and temperature data are processed the same.

9. The system of claim 1 wherein boundaries are determined using the data.

10. A method for determining GW/SW interaction, the method comprising:
    receiving real time data including pressure, fluid conductivity, temperature, and transfer resistance measurements;
    from at least some of the real time data received, simulating the SW/GW interaction to form simulated data;
    fitting the real time data with the simulated data to provide actual SW/GW interaction; and
    determining porosity from Archie's law parameters.

11. The method of claim 10 wherein the transfer resistance data is processed to provide bulk electrical conductivity data.

12. The method of claim 10 wherein the pressure, fluid conductivity, and temperature data are processed the same.

13. The method of claim 10 further comprising processing the data to determine boundaries within the GW.

14. The method of claim 10 further comprising providing iterations of the real time data and fitting each iteration with simulated data.

15. The method of claim 10 further comprising calculating vertical flux from the porosity.

* * * * *